US012653733B2

(12) United States Patent
Patel et al.

(10) Patent No.: US 12,653,733 B2
(45) Date of Patent: Jun. 16, 2026

(54) DISPOSABLE ABSORBENT ARTICLE

(71) Applicant: The Procter & Gamble Company, Cincinnati, OH (US)

(72) Inventors: Sonam Jayanti Patel, Mariemont, OH (US); Edward Paul Carlin, Deerfield Township, OH (US); James William Busch, Maineville, OH (US); Steven Joseph Waas, Mason, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 803 days.

(21) Appl. No.: 17/736,470

(22) Filed: May 4, 2022

(65) Prior Publication Data

US 2022/0354714 A1     Nov. 10, 2022

Related U.S. Application Data

(60) Provisional application No. 63/186,297, filed on May 10, 2021.

(51) Int. Cl.
*A61F 13/537*     (2006.01)
*A61F 13/53*     (2006.01)

(52) U.S. Cl.
CPC .................. *A61F 13/53752* (2013.01); *A61F 2013/530547* (2013.01)

(58) Field of Classification Search
CPC .... A61F 13/53752; A61F 2013/530547; A61F 13/53; A61F 13/535; A61F 2013/53445;
(Continued)

(56) References Cited

U.S. PATENT DOCUMENTS 5,853,402 A     12/1998  Faulks et al.
6,974,892 B2 *  12/2005  DeCarvalho ........ A61F 13/4704
                                                      604/385.03
(Continued)

FOREIGN PATENT DOCUMENTS

EP          0631768 A1     1/1995
EP          2594238 A2     5/2013
(Continued)

OTHER PUBLICATIONS

PCT Search Report and Written Opinion for PCT/US2022/027627 dated Jul. 25, 2022, 12 pages.

*Primary Examiner* — Susan S Su
(74) *Attorney, Agent, or Firm* — Sarah M. DeCristofaro

(57)          ABSTRACT

An absorbent article having a primary topsheet, a backsheet, and an absorbent system therebetween is described. The primary topsheet has a body-facing surface and a garment-facing surface, and the backsheet has a body-facing surface and garment-facing surface. The absorbent system includes a first absorbent core having a body-facing surface and a garment-facing surface, and a second absorbent core disposed between the first absorbent core and the backsheet. The primary topsheet and at least a portion of the first absorbent core has one or more embossed channels including a central channel disposed on the body-facing surface of the primary topsheet. Each of the one or more embossed channels has a bottom surface subjacent to the body-facing surface of the primary topsheet and superjacent to the first absorbent core garment-facing surface.

20 Claims, 8 Drawing Sheets

(58) Field of Classification Search
    CPC .......... A61F 13/51121; A61F 13/15203; A61F
                                  13/53747
    See application file for complete search history.

(56) References Cited

U.S. PATENT DOCUMENTS

| | | |
|---|---|---|
| 2006/0184150 A1 | 8/2006 | Noel |
| 2012/0053547 A1 | 3/2012 | Schroeder et al. |
| 2012/0234475 A1* | 9/2012 | Paldey .............. A61F 13/15731 |
| | | 156/220 |
| 2014/0358106 A1* | 12/2014 | Tan ..................... A61F 13/4752 |
| | | 604/385.01 |
| 2016/0074237 A1 | 3/2016 | Rosati et al. |
| 2018/0098889 A1 | 4/2018 | Hardie |
| 2019/0314211 A1 | 10/2019 | Busch et al. |

FOREIGN PATENT DOCUMENTS

| | | |
|---|---|---|
| JP | 2007267763 A | 10/2007 |
| JP | 2019154670 A | 9/2019 |
| JP | 2019529057 A | 10/2019 |
| JP | 2019198579 A | 11/2019 |
| WO | 0076447 A1 | 12/2000 |
| WO | 2011056205 A1 | 5/2011 |
| WO | 2019200089 A1 | 10/2019 |

* cited by examiner

DISPOSABLE ABSORBENT ARTICLE

CROSS REFERENCE TO RELATED APPLICATION

This application claims the benefit of U.S. Provisional Application No. 63/186,297, filed May 10, 2021, the substance of which is incorporated herein by reference.

FIELD

The present invention pertains to disposable absorbent articles suitable for absorbing and containing body exudates.

BACKGROUND

A variety of disposable absorbent articles have been relied on by consumers to handle or manage body exudates. The users of these absorbent articles can vary widely and may include babies, toddlers, children, teenagers, adults, and elderly persons. So, the types of fluids or body exudates managed by such articles may vary as well to include urine, feces, menses, and other discharges. Typically, in the case of adults, the articles take the form of sanitary napkins, adult incontinence pads, and adult incontinence diapers or undergarments. One of the primary drivers of the desirability of these products to wearers is to give them assurance that when they experience incontinence or other fluid insult event, the occurrence of such will go unnoticed by others and even more ideally by the wearers.

One way of improving the performance and overall discretion of disposable absorbent articles, that has been widely utilized by manufacturers, has been the inclusion of superabsorbent polymers which are able to intake increased amounts of liquid and consequently form a swollen hydrogel material. The resulting hydrogel serves to retain fluid such as discharged body liquids within the structure.

An additional method for improving performance is via the inclusion of embossed channels. Embossed channels can create additional surface area for liquid insults to impinge upon. Additionally, embossed channels can serve as liquid transport pathways which quickly allow fluids to travel to other areas of the absorbent article. However, some materials are not so amenable to embossing. As an example, superabsorbent polymers, can tear through constituent materials when subjected to embossing. This can be undesirable from quality assurance standpoint as well as from a consumer standpoint.

Consequently, there is a need for an absorbent article comprising one or more embossed channels which provides good liquid absorption functionality and reduced likelihood of tearing of the constituent materials.

SUMMARY

Disposable absorbent articles in accordance with the present invention are well suited for providing leakage protection for users that experience relatively small to relatively large discharges of fluids. In one example, absorbent articles of the present disclosure comprise: a primary topsheet having a body-facing surface and a garment-facing surface; a backsheet having a body-facing surface and garment-facing surface; and an absorbent system disposed between the primary topsheet and the backsheet. The absorbent system comprises a first absorbent core having a body-facing surface and a garment-facing surface, and a second absorbent core disposed between the first absorbent core and the backsheet. The first absorbent core comprises a first distribution layer and a first superabsorbent layer, wherein the first superabsorbent layer forms a portion of the garment-facing surface of the first absorbent core, wherein the primary topsheet and the first absorbent core comprise one or more embossed channels including a central channel disposed on the body-facing surface of the primary topsheet, wherein each of the one or more embossed channels comprise a bottom surface subjacent to the body-facing surface of the primary topsheet and superjacent to a garment-facing surface of the first absorbent core.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which the designations are used to designate substantially identical elements and in which:

DETAILED DESCRIPTION

Figure 1:
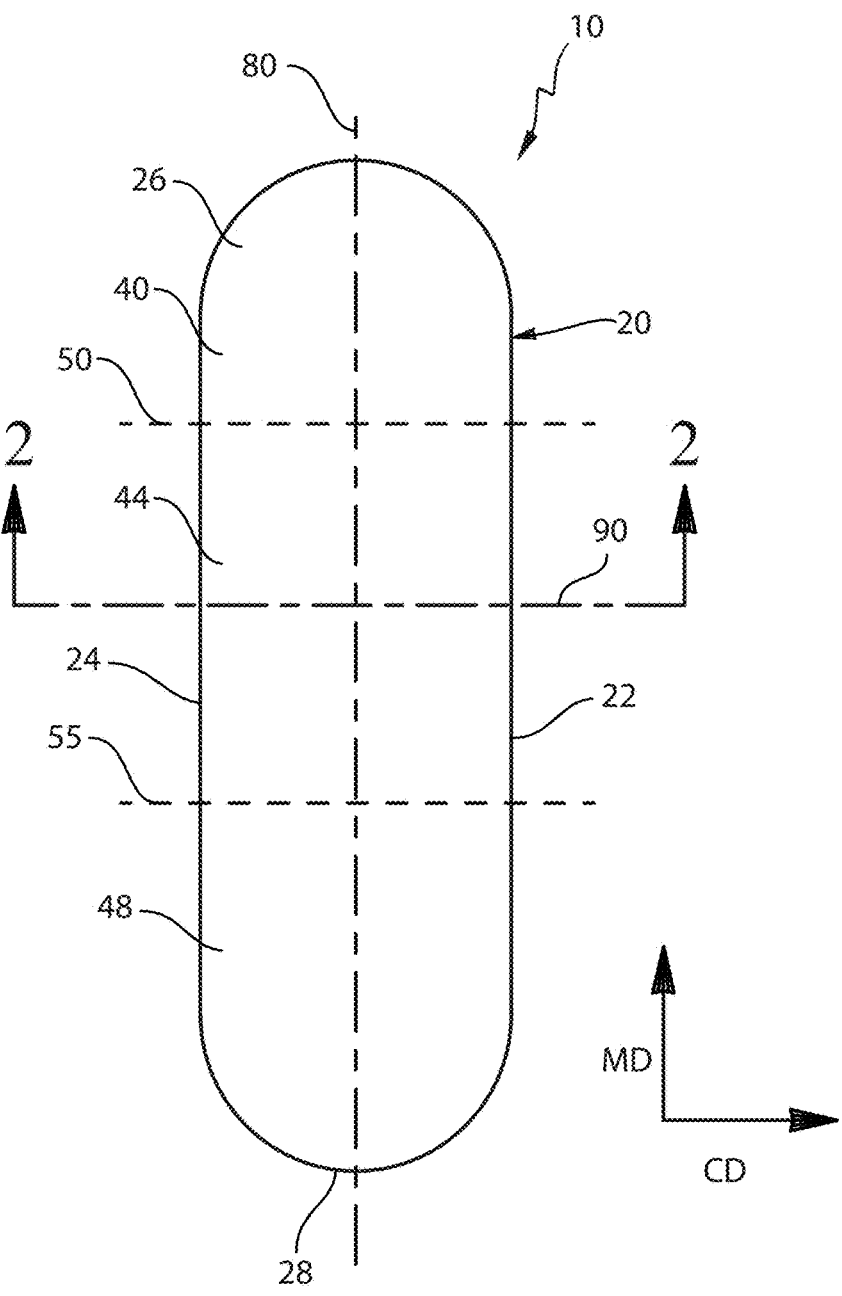
FIG. 1 is a plan view showing an exemplary embodiment of a disposable absorbent article of the present invention, which is an incontinence pad.

The disposable absorbent articles, particularly incontinence pads or pants, of the present invention can provide flexibility to allow for an improved and comfortable fit while reducing the likelihood of tearing and/or providing a rough surface from embossed channels being provided to the absorbent article. In particular, it is envisioned that the articles of the present invention exhibit heightened structural resiliency from the proposed configuration and orientation of the layers contained therein. For the purposes of this disclosure, reference to an incontinence pad, disposable absorbent article, or absorbent article will be used. However, the present invention may be applied to a plurality of absorbent articles including, but not limited to, sanitary napkins, pantiliners, menstrual pads, diapers, training pants, adult incontinence pants, etc.

"Garment-facing surface" as used herein is used to refer to a surface of the absorbent articles of the present disclosure. Specifically, the "garment-facing surface" of the absorbent article is the surface that is closest to the wearer's outer garments during use. Additionally, the term "garment-facing surface" refers to surface of one or more layers in the absorbent articles of the present disclosure where the "garment-facing surface" of the layer(s) are more proximal to the garment-facing surface of the absorbent article than their opposing surface.

"Wearer-facing surface" as used herein is used to refer to a surface of the absorbent articles of the present disclosure. Specifically, the "wearer-facing surface" of the article is the surface that is closest to the wearer during use. Additionally, the term "wearer-facing surface" refers to surfaces of one or more layers in the absorbent articles of the present disclosure, where the "wearer-facing surface" of the layer(s) are more proximal to the wearer-facing surface of the absorbent article than their opposing surface.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

Absorbent articles of the present disclosure comprise a longitudinal centerline and a transverse centerline which is perpendicular to the longitudinal axis. The absorbent articles further comprise a primary topsheet having a wearer-facing surface and an opposing garment-facing surface, a backsheet having a wearer-facing surface and an opposing garment-facing surface, and an absorbent system disposed between the topsheet and the backsheet. The absorbent system comprises a first absorbent core and a second absorbent core.

The first absorbent core may comprise a laminate structure having a wearer-facing surface and an opposing garment-facing surface. The first absorbent core may comprise a first distribution layer and a first superabsorbent layer. In some forms an optional layer may be provided between the topsheet and the first absorbent core. The first distribution layer may be disposed more proximal to the topsheet than the first superabsorbent layer.

The second absorbent core is joined to the garment-facing surface of the first absorbent core. Additionally, the second absorbent core may be configured similar to the first absorbent core. For example, the second absorbent core may comprise a second distribution layer and a second superabsorbent layer. So, the second distribution layer may be attached to the garment-facing surface of the first absorbent core, or the second superabsorbent layer may be attached to the garment-facing surface of the first absorbent core. Alternatively, an additional substrate, e.g. film, nonwoven, woven, the like, or combinations thereof may be provided between the garment-facing surface of the first absorbent core and the second absorbent core.

As noted previously, the absorbent articles of the present disclosure comprise one or more embossed channels. However, the inventors have surprisingly found that embossing of absorbent cores comprising superabsorbent polymer can create problems. It is worth noting that superabsorbent polymer particles comprise rough edges. So, during the embossing process, as a portion of the layers of the absorbent article are compressed, these rough edges can lead to pinhole creation in adjacent layers, e.g. topsheets, and/or can create a rough surface. From the perspective of a wearer, neither pinhole creation in the topsheet nor rough feeling/looking surfaces are desirable.

In an effort to reduce or eliminate the creation of pinholes/rough feeling/rough looking, surface of adjacent layers, e.g. topsheets, the inventors have found that providing superabsorbent polymer containing layers more distal from the topsheet can alleviate the problem. For example, where the topsheet and the first absorbent core are embossed, a secondary topsheet may be provided between the topsheet and the first absorbent core. As another example, where the first absorbent core comprises the first distribution layer and the first superabsorbent layer, the first distribution layer may be disposed more proximal to the topsheet than the first superabsorbent layer. Furthering this example, the first distribution layer may be disposed between the secondary topsheet and the first superabsorbent layer.

In such examples, where the topsheet and the first absorbent core are embossed, the wearer-facing surface of the absorbent article comprises a depressed channel. The depressed channel can have a bottom surface which is subjacent to the remainder of the wearer-facing surface of the absorbent article. The bottom surface can be superjacent to the garment-facing surface of the first absorbent core. These one or more embossed channels can provide preferential bending axes for the pad to provide better fit and reduce the likelihood of leakage. Additionally, these embossed channels, as they are highly densified areas of material, can serve as pathways to assist in distributing liquid insults to areas of the absorbent system that would otherwise have to rely on a distribution layer to wick moisture to areas more distal from the area of initial liquid insult.

Where the first absorbent core comprises the first superabsorbent layer and the first distribution layer, both layers may be embossed. However, in order to further reduce the likelihood of the superabsorbent polymer rough edges from creating pinholes and/or creating a rough feeling/rough looking wearer-facing surface of the article, only a portion of the first absorbent core may be embossed. For example, the first distribution layer may be embossed together with the topsheet while the first superabsorbent layer is not subjected to this embossing process. In such configurations, the embossed channels can have a bottom surface which is superjacent to the wearer-facing surface of the first superabsorbent layer.

In addition to the embossed channels on the wearer-facing surface, the first absorbent core and topsheet may comprise one or more second embossed channels on the garment-facing surface of the first absorbent core. For example, the one or more second embossed channels may extend from the garment-facing surface of the first absorbent core toward the topsheet. A bottom surface (or top surface) of the one or more second embossed channels may be subjacent to the wearer-facing surface of the topsheet.

It is worth noting that in addition to the first absorbent core being embossed as described herein, the second absorbent core may similarly be embossed. However, care should be taken when choosing such configurations. The embossing process, while creating desired bending axes and beneficial fluid pathways, can also reduce the amount of void volume in the absorbent system. This loss of void volume can mean reduced capacity of the absorbent article. Particularly in the context of adult incontinence articles, embossing of the second absorbent core to the same extent as the first absorbent core could be problematic without accounting for the loss of void volume due to the embossing process. So, configurations of the absorbent articles of the present disclosure are contemplated where the second absorbent core does not comprise embossed channels or at least does not comprise the embossed channels to the same extent as the first absorbent core.

For example, the second absorbent core may comprise area of embossing than the first absorbent core. As another example, the second absorbent core may comprise embossing which does not comprise the same depth as the embossing that is present in the first absorbent core.

Additionally, forms are contemplated where the second absorbent core may be embossed while the first absorbent core is not embossed. Such configurations can provide many of the same benefits as the embossing of the first absorbent core versus the second absorbent core. However, as the second absorbent core is disposed between the backsheet and the first absorbent core, the second absorbent core is the final storage layer for liquid insults. So, the void volume of the second absorbent core can impact the ultimate absorbent capacity of the overall absorbent article. Moreover, emboss-ment of the second absorbent core may not be visible to users of the absorbent article. So, the additional functionality of embossment may not be readily perceivable by users as the embossment is not visible.

As noted previously, the second absorbent core may be configured similar to that of the first absorbent core, e.g. having a second distribution layer and a second superabsorbent layer. The absorbent system may be configured such that the second distribution layer is joined to the garment-facing surface of the first absorbent core while the second superabsorbent layer is joined to the backsheet or at least positioned more proximal to the backsheet than the second distribution layer. Alternatively, the second superabsorbent layer may be joined to the garment-facing surface of the first absorbent core while the second distribution layer is joined to the backsheet or positioned more proximal to the back-sheet than the second superabsorbent layer.

While not wishing to be bound by theory, it is believed that when the superabsorbent layer is positioned adjacent or more proximal to the backsheet the risk of the creation of pinholes in the backsheet increases. Recall that superabsor-bent polymer particles have rough edges in their dry state. These rough edges can cause pinholes in backsheets, par-ticularly where the backsheet film is relatively thin. The creation of pinholes can increase the likelihood of leakage. And even where these rough edges do not create pinholes in the backsheet, these rough edges can cause the backsheet to feel rough to the touch and create a very bumpy visual appearance. This can be displeasing to the wearer of the absorbent article. So, where thinner backsheets are desired, it may be beneficial to configure the second absorbent core such that the second superabsorbent layer is joined to the garment-facing surface of the first absorbent core. In such configurations, the second distribution layer is disposed between the backsheet and the second superabsorbent layer which can reduce the likelihood of the creation of pinholes in the backsheet via the superabsorbent polymer. Alterna-tively, or in conjunction with the foregoing, the rough feel of the backsheet may be overcome by providing a nonwoven material on the garment-facing surface of the backsheet. This outer nonwoven can decrease the rough feel and/or look of the backsheet.

It is worth noting that an optional fluid management layer may be provided between the primary topsheet and the first absorbent core. An example includes a secondary topsheet which is known in the art. Suitable examples of secondary topsheets are discussed in additional detail hereafter.

The first absorbent core and the second absorbent core may be joined together in an offset manner. For example, the first absorbent core may be disposed such that it forms a front end portion of the absorbent system while the second absorbent core is disposed such that it forms a rear end portion of the absorbent system. Where the first absorbent core and the second absorbent core overlap, a central portion is formed. Additionally, the first absorbent core and the second absorbent core may comprise machine direction lengths which are the same. Alternatively, the first absorbent core and the second absorbent core may comprise machine direction lengths which are different.

In addition to being joined in an offset manner or inde-pendently thereof, the first absorbent core and the second absorbent core can have varying widths parallel to a trans-verse axis of the absorbent article. For example, the first absorbent core and the second absorbent core may comprise widths which are equal to one another. Alternatively, the first absorbent core and the second absorbent core can have different cross direction widths. For example, the first absor-bent core may have a cross direction width which is less than the width of the second absorbent core. The first absorbent core may have a cross directional width which is less than about 95 percent of the width of the second absorbent core, more preferably less than about 90 percent, or most prefer-ably less than about 85 percent of the cross directional width of the second absorbent core, specifically reciting all values within these ranges and any ranges created thereby. As a further example, the first absorbent core can have a cross directional width that is from about 50 percent to about 95 percent the width of the second absorbent core, more pref-erably from about 50 percent to about 90 percent the width of the second absorbent core, or most preferably from about 50 percent to about 85 percent the width of the second absorbent core, specifically reciting all values within these ranges or any ranges created thereby.

Where the first absorbent core has a smaller width than does the second absorbent core, improved fit can be accom-plished. For example, where longitudinal side edges of the first absorbent core are disposed inboard of the longitudinal side edges of the second absorbent core, the absorbent article can preferentially bend in areas laterally outboard of the longitudinal side edges of the first absorbent core. This preferential bending can increase the comfort of the absor-bent article while also improving the absorbent articles resistance to leakage.

The absorbent articles of the present disclosure are now further described with reference to the FIGS. described herein. FIG. 1 shows an absorbent article of the present disclosure or more particularly an incontinence pad or sanitary napkin 10 (referred to mainly as "incontinence pad" herein) may comprise a longitudinal axis 80 and a lateral axis 90. The longitudinal axis 80 generally extends parallel to the longest dimension of the incontinence pad 10. The lateral axis 90 extends generally perpendicular to the lon-gitudinal axis 80 and lies in the same plane as the inconti-nence pad 10 in a flattened state on a flat surface. The lateral axis 90 bisects the length of the incontinence pad 10 where the length is parallel to the longitudinal axis 80, and the longitudinal axis 80 bisects the width of the incontinence pad 10 where the width is parallel to the lateral axis 90. Additionally, as shown, the MD direction may be generally parallel to the longitudinal axis 80 of the incontinence pad 10, and the CD direction may be generally parallel to the lateral axis 90.

The incontinence pad 10 comprises a generally elongated oval shape. However, any suitable shape may be utilized. Some examples include hourglass (peanut), offset hourglass (one end is wider than an opposite end and a narrowed mid-section between the ends), etc. The incontinence pad 10 may be symmetric about the longitudinal axis 80 or asym-metric about the longitudinal axis 80. Similarly, the incon-tinence pad 10 may be symmetric about the lateral axis 90 or asymmetric about the lateral axis 90.

The incontinence pad 10 may further comprise a chassis 20 comprising a plurality of side edges 22 and 24 which extend generally parallel to the longitudinal axis 80. A pair of end edges 26 and 28 join each of the side edges 22 and 24. One end edge 26 joins the side edges 22 and 24 in the first end region 40 of the incontinence pad 10 while the other end edge 28 joins the side edges 22 and 24 in the second end region 48 of the incontinence pad 10—the second end region 48 being opposite the first end region 40. An intermediate region 44 is disposed between the first end region 40 and the second end region 48.

Figure 2:
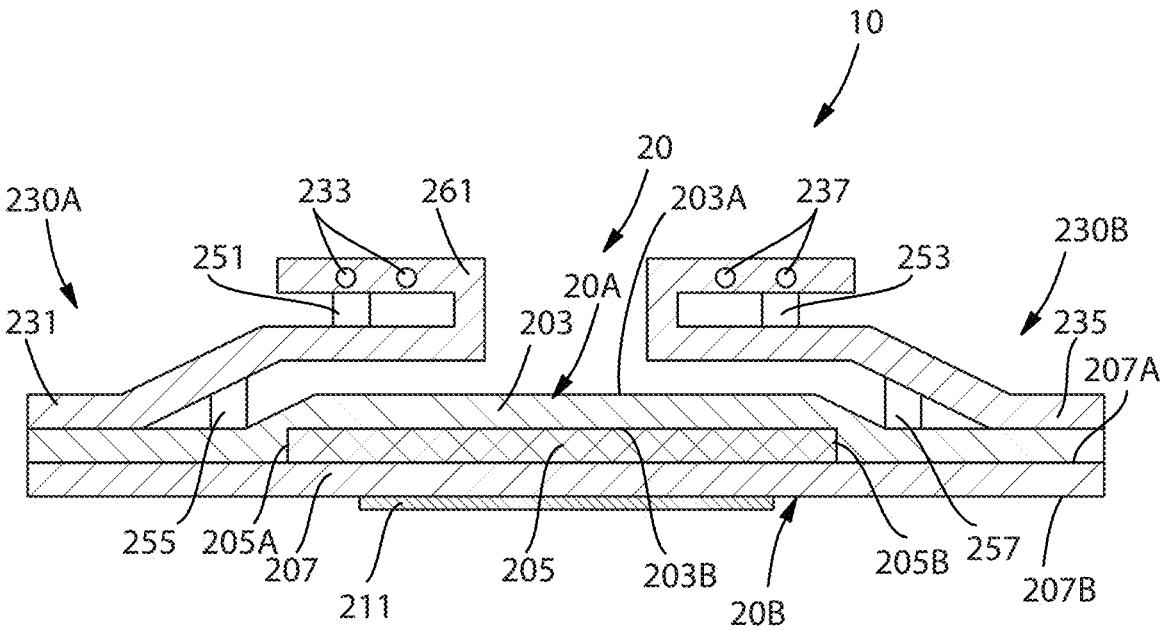
FIG. 2 is a cross-sectional view of the incontinence pad shown in FIG. 1 taken along 2-2.

The chassis 20 of FIG. 1 is shown in cross-section in FIG. 2. Among other things, the chassis 20 comprises a primary topsheet 203. This primary topsheet has a wearer-facing surface 203A and a garment-facing surface 203B. This chassis 20 of the pad 10 further comprises a backsheet 207 which also comprises its own wearer-facing surface 207A and opposing garment-facing surface 207B. These two components sandwich an absorbent system 205. In other words, the absorbent system 205 is disposed between the topsheet 203 and the backsheet 207. All three components (i.e., topsheet 203, backsheet 207, and absorbent system 205) form the chassis 20 of the pad 10. Additional layers may very well be included within this chassis 20, particularly between the topsheet 203 and the backsheet 207 but it should be noted that these layers are separate and apart from the absorbent system. Suitable additional layers may include secondary topsheets, acquisition layers, additional distribution layers over and above those which will be discussed below, and other useful layers. In the case of a secondary topsheet, it is disposed beneath the primary topsheet 203 and on the body-facing surface of the system. In certain embodiments, the secondary topsheet (also known as the "STS") has a greater length and width than the absorbent system 205.

The chassis 20 further comprises a wearer-facing surface 20A and a garment-facing surface 20B. The wearer-facing surface 20A may comprise the topsheet 203, and the garment-facing surface 20B may comprise the backsheet.

Figure 3:
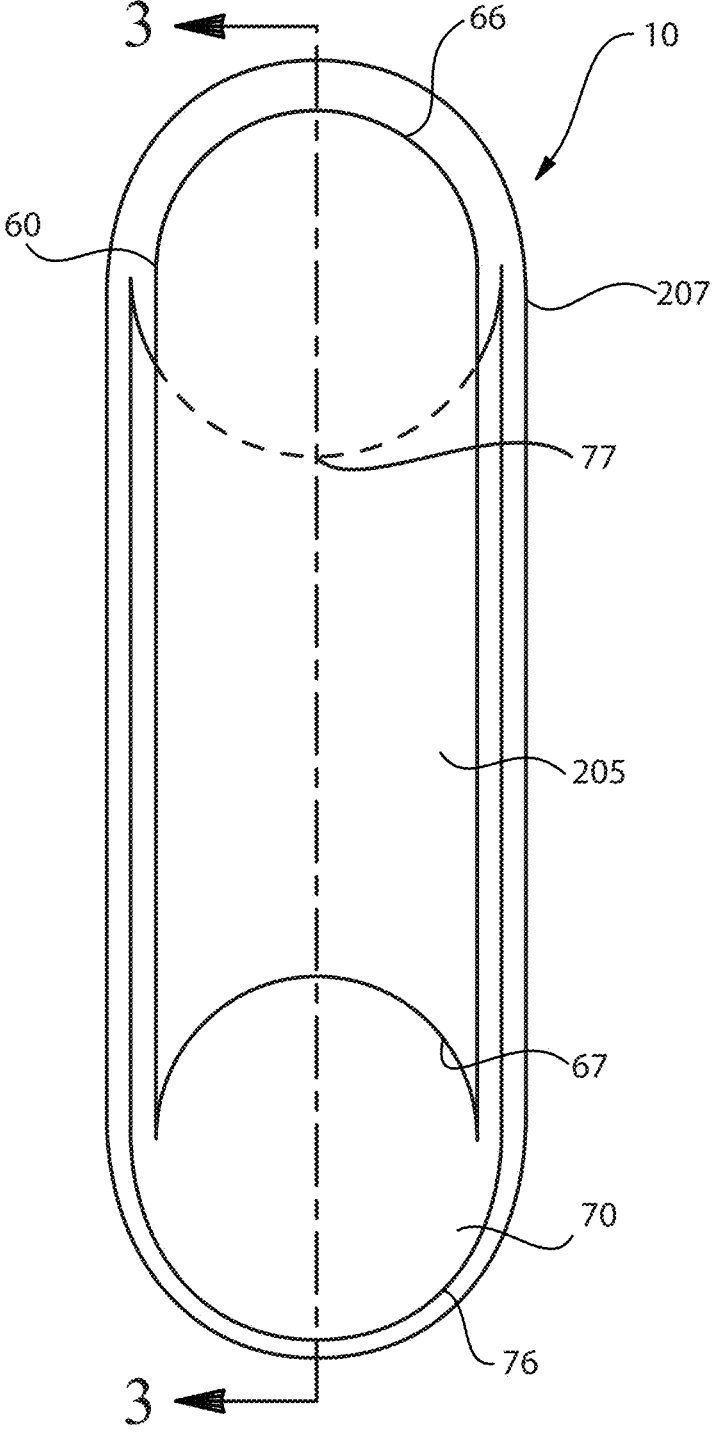
FIG. 3 is a plan view of the pad of FIG. 1 with the primary topsheet removed.
Figure 4:
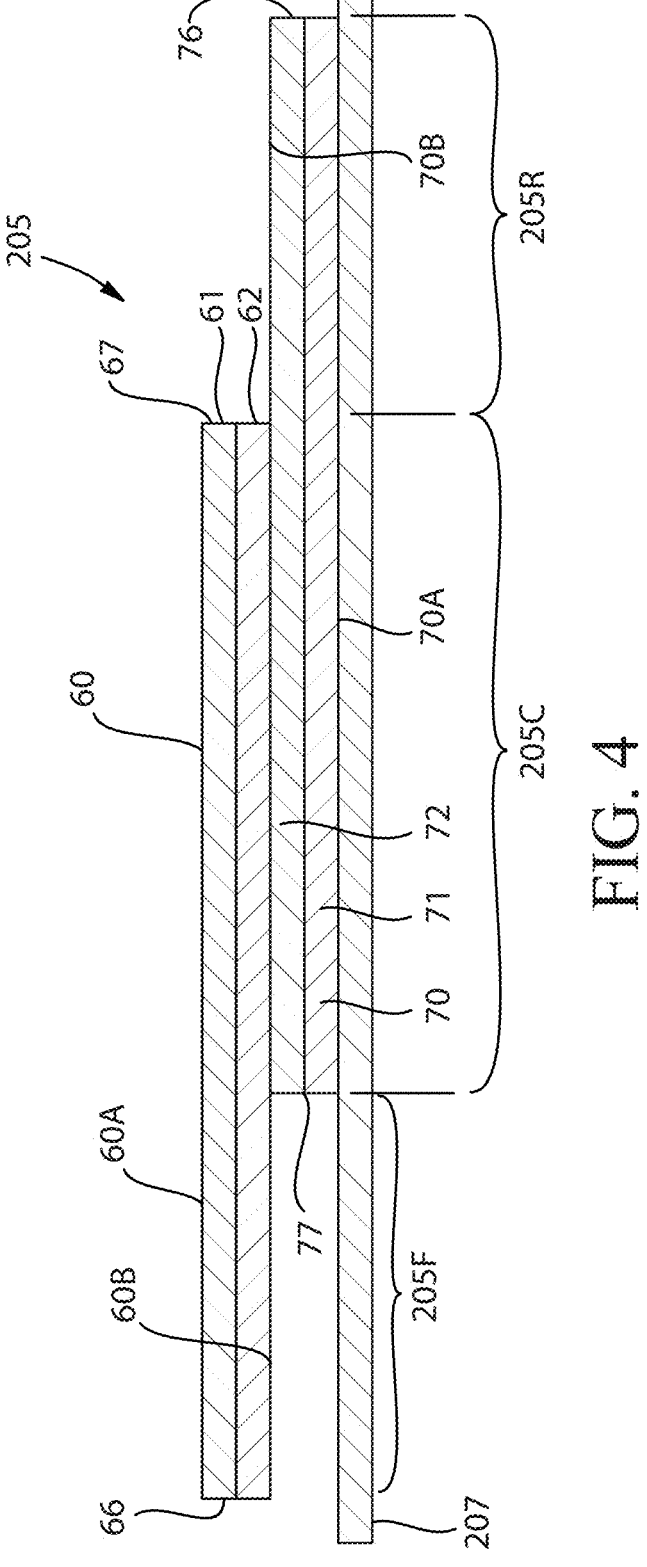
FIG. 4 is a cross-sectional view of the absorbent core of the pad of FIG. 3 taken along 3-3.

The absorbent system 205 is formed from multiple layers and is directed to quickly acquiring the bodily fluid or exudates and distributing them along a length of the system. FIG. 3 depicts an absorbent system in accordance with the present disclosure as it shows a plan view of the pad 10 with the primary topsheet 203 removed for viewing of the absorbent system 205 positioned above the backsheet 207. FIG. 4 shows a cross-section of this absorbent system 205 in more detail. The absorbent system 205 may comprise a first absorbent core 60 which may include a first superabsorbent layer 61 disposed on a first distribution layer 62. The first absorbent core 60 has a wearer-facing surface 60A and a garment-facing surface 60B which opposes the upper surface. Additionally, the first absorbent core 60 has a first end 66 and a second end 67 which opposes the first end 66.

The absorbent system 205 may further comprise a second absorbent core 70 which may include a second superabsorbent layer 71 and a second distribution layer 72. This second absorbent core 70 also has a wearer-facing surface 70A and a garment-facing surface 70B, a first end 76, and a similar opposing second end 77. In the embodiment of FIGS. 3 and 4, the first distribution layer 62 is joined to the second distribution layer 72 in an offset manner or configuration along the length of the system. In such configurations, as noted previously, care should be taken when exposing the first absorbent core to an embossing process as the first superabsorbent layer 61 is more proximal to the primary topsheet than the first distribution layer 62.

In another configuration, the second absorbent core 70 may be joined to the first superabsorbent layer 61 instead of the first distribution layer. In this instance, the laminates may be joined to one another in an offset manner as well except the first superabsorbent layer 61 may be joined to either the second superabsorbent layer 71 or the second distribution layer 72.

As used herein "offset" or "offset manner" means that the layers or laminates of interest are staggered and that their respective first ends or second ends are not aligned in the z-direction (i.e., the first end of one layer or absorbent core is not coterminous with the second end of an adjacent underlying or overlying layer or laminate) when the layers or laminates overlay one another. This offset joinder of the first and second distribution layers 62, 72 results in an overlapping and joined area of the two absorbent cores that forms a central portion 205C of the absorbent system 205. The central portion 205C of the system is consequently bounded on each side by a front end portion and a rear end portion 205R, both of the system. In other words, the front end portion 205F and the rear end 205R portion are respectively disposed at opposing ends of the system 205. The front end portion 205F is formed from a first end 66 or second end 67 of the first absorbent core 60 while the rear end portion 205F of the system 205 is formed by the first end 76 or second end 77 of the second absorbent core 70. In the embodiment of FIG. 3, the first ends 66, 76 of the first and second absorbent cores oppose each other and form a front end portion 205F and a rear end portion 205R of the absorbent system 205, respectively. In an alternate embodiment, the second ends 67, 77 of the first and second absorbent cores may oppose each other and form a front end portion 205F and a rear end portion 205R of the absorbent system 205, respectively. In both instances, the first ends 66, 76 are in the form of a male connection derived from a nested cut of the first and second absorbent cores. Similarly, the second ends 67, 77 are in the form of a female connection derived from a nested cut of the first and second absorbent cores, respectively.

In one embodiment, the overlapping area or region that forms the central portion 205C of the system 205 can have at least one characteristic of a greater capacity, a greater void volume, or a greater thickness than the front end portion 205F and the rear end portion 205F of the absorbent system 205. This embodiment is particularly useful for providing for heightened leakage protection in the central portion where female users of such pads would typically contact the pad and release fluids.

Article Length

Over and above the elemental portions described herein, the absorbent articles of the present disclosure may exhibit a range of article lengths to accommodate a wide variety of user body sizes and situations, e.g. day versus night-time use. For example, a small pad may have a length from between about 250 mm to about 329 mm according to the Article Length Method. In certain embodiments, the article length is greater than 250 mm, 255 mm, 260 mm, and 265 mm and less than 329 mm, 325 mm, 315 mm, 305 mm, 295 mm, 285 mm, and 275 mm. An intermediate sized pad may comprise a pad length of from about 330 mm to about 370 mm according to the Article Length Method. In certain embodiments, the article length is greater than 330 mm, 335 mm, 340 mm, and 345 mm and less than 370 mm, 365 mm, 360 mm, 355 mm, and 350 mm. In an embodiment, the article length is about 348 mm. And a large pad may exhibit an article length of from about 371 mm to about 500 mm according to the Article Length Method. In certain embodiments, the article length is greater than 371 mm, 380 mm, 390 mm, and 395 mm and less than 500 mm, 490 mm, 480 mm, 470 mm, 460 mm, 450 mm, 440 mm, 430 mm, 420 mm, and 410 mm. In an embodiment, the article length is about 400 mm. he length of the disposable absorbent article is important for a variety of reasons.

First, the article must be of sufficient length to cover the intended area of insult that the article is likely to experience during use. This means that to the extent a consumer expects that the fluids dispelled during the time of article wear are relatively minimal due since the product is being worn during the daytime and there is easier access to toilet facilities, a shorter pad may suffice. Additionally, a shorter pad may also be more suitable during the day when the wearer's body is in a seated or standing position and the area of insult is almost orthogonal to the area of fluid expulsion, i.e., the genitalia. As a wearer's absorbency needs increase for reasons such as inaccessibility to toilet facilities, heightened inability to control urine events due to decreased mobility or weakened bladder control, it is likely desirable to increase the pad length to allow for incorporation of more absorbent material and a greater area of coverage where expelled fluids may be retained. Additionally, a disposable absorbent article that is worn at night or while a wearer is in a bed tends to be of the longest pad length. This is typically the case for since the wearer may not be able to react as quickly as required to reach the toilet facilities in a timely fashion if sleeping or laying down. Moreover, as a wearer is laying down and fluids are expelled, there is usually a tendency of the expelled fluids to creep farther along the length of the pad due to the gravitational pull on the fluid along the surface of the genital area to the gluteal area if she is laying on their back or to the groin if she is laying on their stomach. It should be noted that although article length may typically be assumed to correspond to a pad type product, it is envisioned herein that such a pad could very well be integrated into a pant product that may be worn in place of underwear.

Emboss Pattern

As noted previously, several layers of the absorbent articles of the present disclosure may be embossed together. Any suitable emboss pattern may be utilized. As an example, a suitable emboss pattern may comprise generally arcuate channels. These generally arcuate channels may comprise opened ends or closed ends. Within these channels, areas of highly compressed areas may alternate with lower compressed areas. A central channel can substantially surround a central area of the article allowing for adequate width between adjacent channels in an area of expected fluid insult.

Larger pads may allow for additional channels. For example, some absorbent articles may comprise a front region channel and/or a rear region channel. The front region channel and/or rear region channel can comprise arcuate channels much like the central channel. And in order to smooth the look of the central channel, the front region channel and/or rear region channel may comprise a larger radius of curvature than adjacent ends of the central channel. This can provide a much more rounded look to the overall emboss pattern. Some suitable emboss patterns for use with the absorbent articles of the present disclosure are discussed in additional detail in U.S. Patent Application Publication Nos. US2007/0005036, US2005/0124951, and US2006/0116653.

As noted previously, while the embossed channels can provide many fluid acquisition/distribution benefits, the embossed channels can also provide visual cues to the user. Specifically, central channel can encompass, at least in part, the area of intended fluid entry of the pad. So channels of the present disclosure can increase in length with an increase in pad length. For example, in the smaller sizes, e.g. about 330 mm or less in length, the central channel may comprise a length which is 53 percent or less than the overall length, more preferably about 50 percent or less, or most preferably about 47 percent or less than the overall length of the pad, specifically reciting all values within these ranges and any ranges created thereby. For example, the central channel may comprise a length of from between about 25 percent to about 53 percent of the overall length, more preferably from about 30 to about 50 percent of the overall length or most preferably from about 35 percent to about 47 percent of the overall length of the pad, specifically reciting all values within these ranges and any ranges created thereby.

For larger sizes, greater than about 330 mm, the length of the overall embossed pattern, i.e. the central channel, the front region channel and the rear region channel, may have a length which is 80 percent or less, more preferably about 75 percent or less or most preferably about 70 percent or less of the overall length of the pad, specifically reciting all values within these ranges and any ranges created thereby. For example, the embossed pattern of the present disclosure may comprise an overall length of from about 30 percent to about 80 percent, about 40 percent to about 75 percent or most preferably about 50 percent to about 70 percent of the overall length of the pad, specifically reciting al values within this range and any ranges created thereby.

Figure 6:
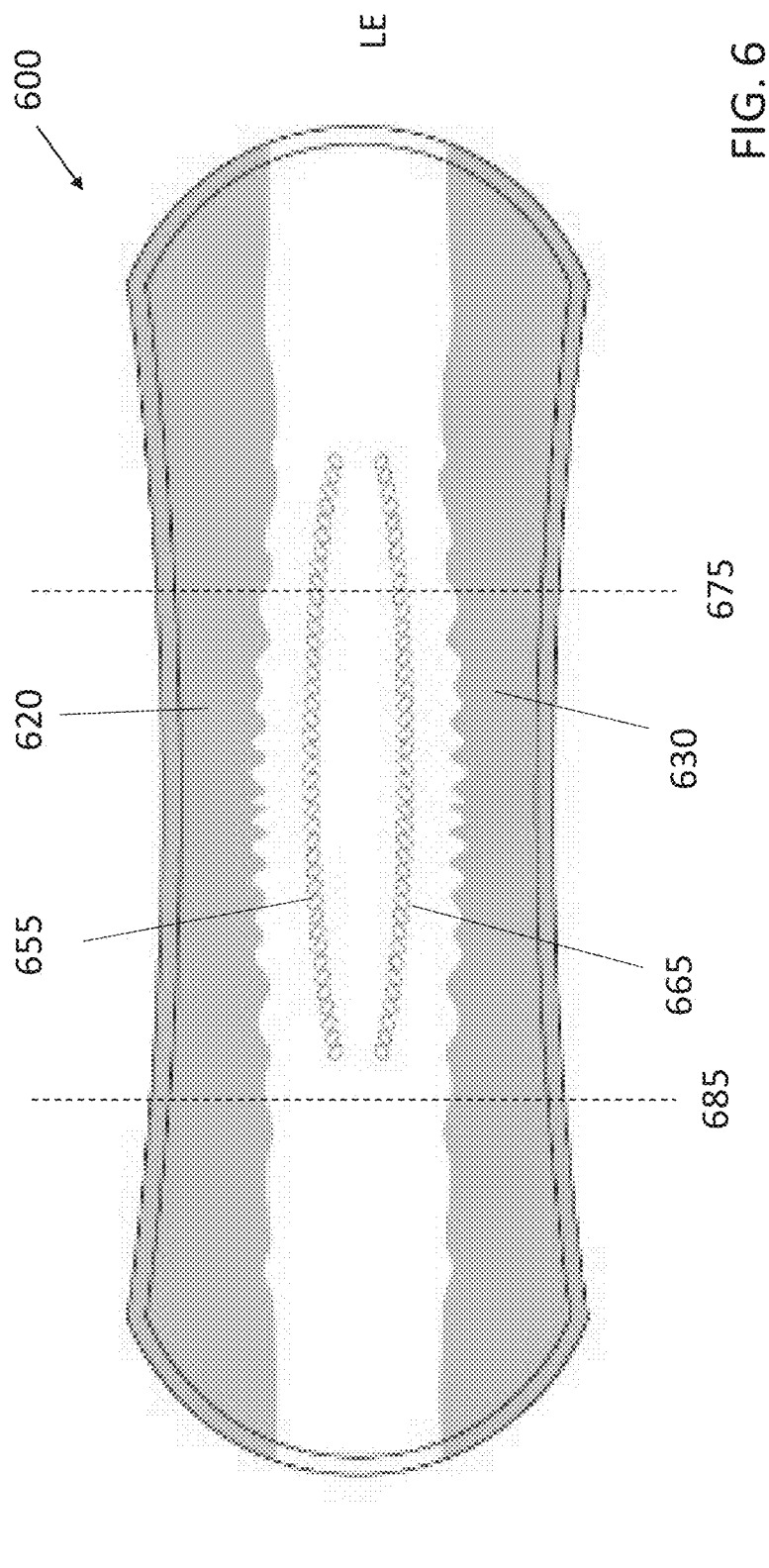
FIG. 6 is a schematic representation of an exemplary absorbent article of the present disclosure.
Figure 7:
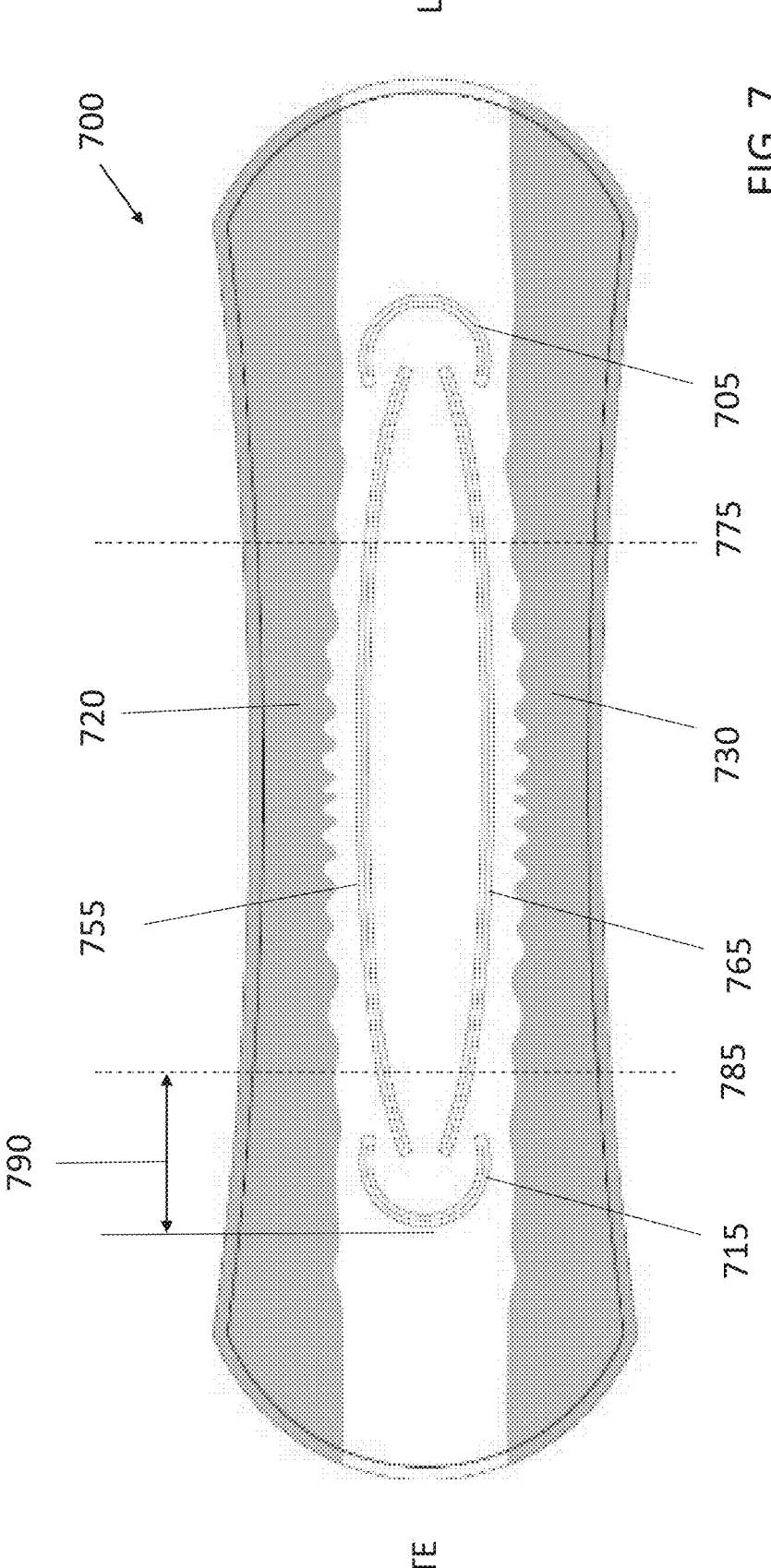
FIG. 7 is a schematic representation of an exemplary absorbent article of the present disclosure.
Figure 8:
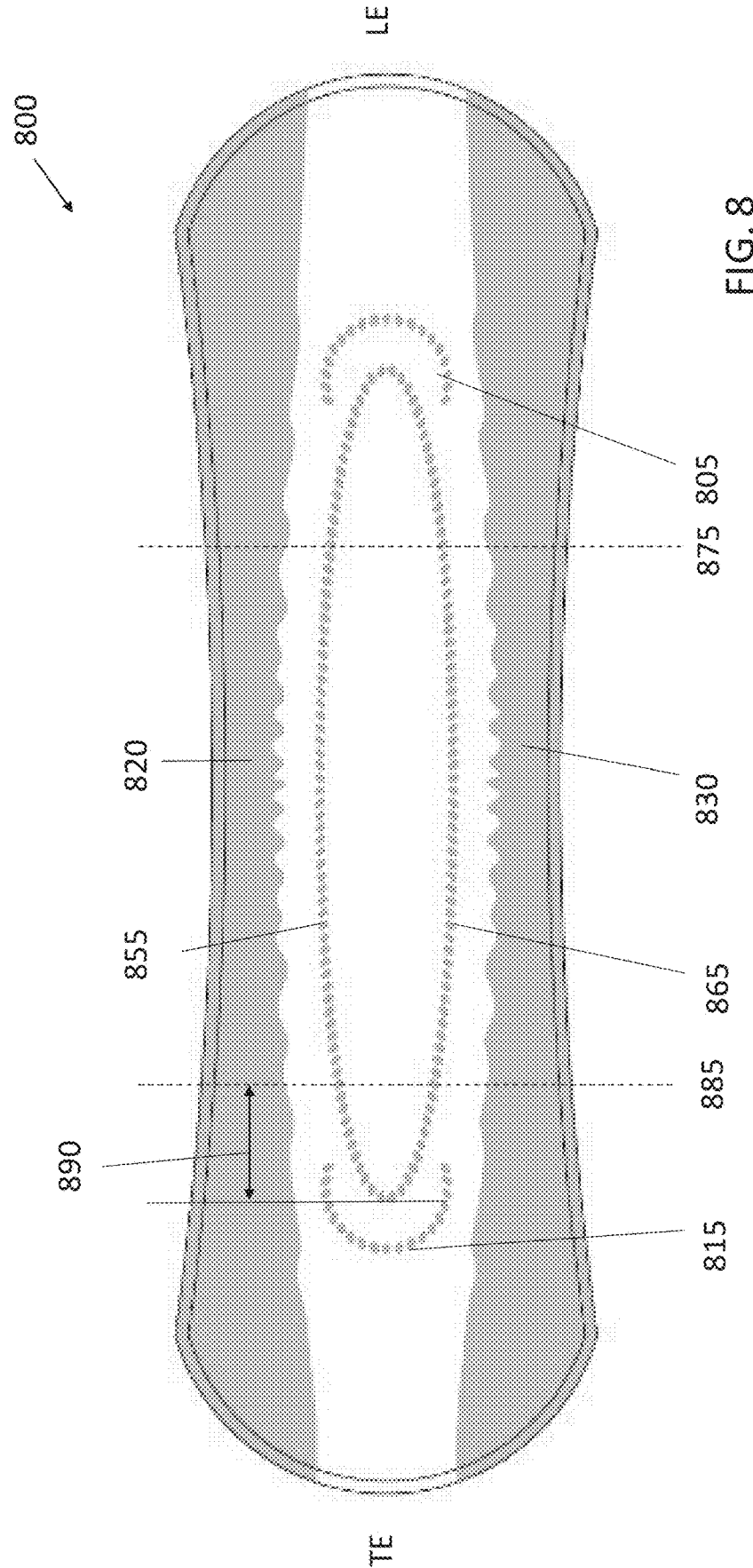
FIG. 8 is a schematic representation of an exemplary absorbent article of the present disclosure.

FIGS. 6-8 show absorbent articles comprising exemplary emboss patterns. Referring specifically to FIG. 6, an absorbent article 600 comprising a central channel is shown. The central channel may comprise a first portion 655 and a second portion 665. The first portion 655 and the second portion 665 may be mirror images of each other, i.e. symmetrical about a longitudinal axis of the absorbent article 600. However, as noted previously, where only the first absorbent core is embossed and where the first absorbent core and the second absorbent core are offset from one another, the first portion 655 and the second portion 665 may not be symmetrical about a transverse axis of the absorbent article 600. For example, as shown the central channel may be offset such that a larger percentage of the emboss pattern is more proximal to a leading edge ("LE") side than a trailing edge ("TE") side.

The first portion 655 and second portion 665 are disposed between opposing leg cuffs 620 and 630. Additionally, fold lines 675 and 685 may be positioned such that the first portion 655 and the second portion 665 overlap the fold line 675 but do not overlap the second fold line 685.

As shown in FIG. 7, an absorbent article 700 comprises a central channel having a first portion 755 and a second portion 765. Additionally, the absorbent article 700 may comprise a front region channel 705 and a rear region channel 715. As shown, a radius of curvature of both the front region channel 705 and the rear region channel 715 is greater than a radius of curvature for ends of the central channel. In this specific example, the first portion 755 and the second portion 765 are not joined at their respective ends; however, a projected radius of the first portion 755 and the second portion 765 joined at their ends would be less than the radius of the front region channel 705 and the rear region channel 715. Such configurations can provide the embossed pattern on the absorbent article 700 a more rounded look overall.

Similar to the absorbent article of FIG. 6, each of the central channel, front region channel 705 and rear region channel 715 are disposed between opposing leg cuffs 720 and 730. Additionally, fold lines 775 and 785 may be configured such that they overlap the central channel. It is worth noting that as noted previously, embossed channels may create preferential bending axes. So, it is believed that where fold lines are placed too close to emboss channels which extend in a transverse direction, the folding of the article may not be as desired. For example, it is believed that where the fold line is too close to the transversely extending embossed channel, the folding of the article may be a bit blurred in this area and not occur on the fold line. So, it is believed that the fold lines should be spaced from transversely extending portions of emboss channels by at least 5 mm. For example, it is believed that a distance 790 between an apex of the rear region channel 715 and the fold line 785 should be at least 5 mm. It is believed that the same would hold true for a distance between an apex of the front region channel 705 and the fold line 775.

As shown in FIG. 8, an absorbent article 800 comprises a central channel having a first portion 855 and a second portion 865. Additionally, the absorbent article 800 may comprise a front region channel 805 and a rear region channel 815. As shown, a radius of curvature of both the front region channel 805 and the rear region channel 815 is greater than a radius of curvature for ends of the central channel. Such configurations can provide the embossed pattern on the absorbent article 700 a more rounded look overall.

In this specific example, the first portion 855 and the second portion 865 are joined at their respective ends. So unlike the first and second portions of FIGS. 6 and 7, the first and second portions, 855 and 865, respectively, are not discrete channels. Rather each of the first portion 855 and second portion 865 are joined at their ends.

Additionally, each of the central channel, front region channel 805 and rear region channel 815 are disposed between opposing leg cuffs 820 and 830. And similar to FIG. 7, fold lines 875 and 885 may be configured such that they overlap the central channel. And similar to FIG. 7, it is believed that where the ends of the first portion 855 and the second portion 865 are joined, a transversely extending portion of the channel is created. It is further believed that a distance 890 between an apex of the first portion 855 and second portion 865 and the fold line 885 should be at least 5 mm.

In order to maintain a "clean" fold line which folds in a desired area, the distances between a fold line and a transverse portion of an emboss channel or emboss element can be at least 5 mm. However to accommodate variability in manufacturing tolerances, the distance can be at least 5 mm, more preferably at least 7 mm, or most preferably at least 9 mm, specifically reciting all values within these ranges and any ranges created thereby.

Dry Pad Thickness

In conjunction with the abovementioned properties, the articles of the present invention also exhibit a dry pad thickness of between about 4.4 mm to about 9.5 mm according to a Pad Thickness Method. As mentioned relative to the desirable acquisition time, it is important to the consumer that she be able to wear her disposable absorbent product with confidence in its absorbency performance. Almost as critical as absorbency to her is the concept of the article being discreet. This means that the consumer would like to wear the article without it being noticeable by others and without a constant reminder to herself that she is wearing it because she needs to wear it. From this perspective, it is desirable that the article be as thin as feasible. Therefore, the articles of the present invention exhibit a dry pad thickness of greater than about 5 mm, 5.5 mm, or 6 mm and less than about 9 mm, 8.5 mm, 8 mm, 7.5 mm, 7 mm, or 6.5 mm.

Primary Topsheet

The primary topsheet 203 (also referred to herein "topsheet") of the chassis 20 is positioned adjacent a body-facing surface 203A of the absorbent system 205 and may be joined thereto and to the backsheet 207 by attachment methods (not shown) such as those well known in the art. Suitable attachment methods are described with respect to joining the backsheet 207 to the absorbent system 205. The topsheet 203 and the backsheet 207 may be joined directly to each other in the incontinence pad periphery and may be indirectly joined together by directly joining them to the absorbent system 205 or additional optional layers within the chassis like a secondary topsheet which spans the entire or partial area of the article. This indirect or direct joining may be accomplished by attachment methods which are well known in the art.

The absorbent article may comprise any known or otherwise effective primary topsheet, such as one which is compliant, soft feeling, and non-irritating to the wearer's skin. Suitable primary topsheet materials include a liquid pervious material that is oriented towards and contacts the body of the wearer permitting bodily discharges to rapidly penetrate through it without allowing fluid to flow back through the topsheet to the skin of the wearer. The primary topsheet, while being capable of allowing rapid transfer of fluid through it, also provides for the transfer or migration of the lotion composition onto an external or internal portion of a wearer's skin. A suitable topsheet can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof.

Apertured film materials suitable for use as the topsheet include those apertured plastic films that are non-absorbent and pervious to body exudates and provide for minimal or no flow back of fluids through the topsheet. Nonlimiting examples of other suitable formed films, including apertured and non-apertured formed films, are more fully described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,342,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986. Commercially available formed filmed topsheets include those topsheet materials marketed by the Procter & Gamble Company (Cincinnati, Ohio) under the DRI-WEAVE® tradename.

Nonlimiting examples of woven and nonwoven materials suitable for use as the topsheet include fibrous materials made from natural fibers, modified natural fibers, synthetic fibers, or combinations thereof. These fibrous materials can be either hydrophilic or hydrophobic, but it is preferable that the topsheet be hydrophobic or rendered hydrophobic. As an option, portions of the topsheet can be rendered hydrophilic, by the use of any known method for making topsheets containing hydrophilic components. One such method include treating an apertured film component of a nonwoven/apertured thermoplastic formed film topsheet with a surfactant as described in U.S. Pat. No. 4,950,264, issued to Osborn on Aug. 21, 1990. Other suitable methods describing a process for treating the topsheet with a surfactant are disclosed in U.S. Pat. Nos. 4,988,344 and 4,988,345, both issued to Reising et al. on Jan. 29, 1991. The topsheet may have hydrophilic fibers, hydrophobic fibers, or combinations thereof.

A particularly suitable topsheet comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

When the primary topsheet comprises a nonwoven fibrous material in the form of a nonwoven web, the nonwoven web may be produced by any known procedure for making nonwoven webs, nonlimiting examples of which include spunbonding, carding, wet-laid, air-laid, meltblown, needle-punching, mechanical entangling, thermo-mechanical entangling, and hydroentangling. A specific example of a suitable meltblown process is disclosed in U.S. Pat. No. 3,978,185, to Buntin et al., issued Aug. 31, 1976. The nonwoven may be compression resistant as described in U.S. Pat. No. 7,785,690 entitled "Compression Resistant Nonwovens" issued on Aug. 31, 2010. The nonwoven web may have loops as described in U.S. Pat. No. 7,838,099 entitled "Looped Nonwoven Web" issued on Nov. 23, 2010.

Other suitable nonwoven materials include low basis weight nonwovens, that is, nonwovens having a basis weight of from about 18 g/m² to about 25 g/m². An example of such a nonwoven material is commercially available under the tradename P-8 from Veratec, Incorporation, a division of the International Paper Company located in Walpole, Mass. Other nonwovens are described in U.S. Pat. Nos. 5,792,404 and 5,665,452.

The topsheet may comprise tufts as described in U.S. Pat. No. 8,728,049 entitled "Absorbent Article Having a Tufted Topsheet" issued on May 20, 2014, U.S. Pat. No. 7,553,532 entitled "Tufted Fibrous Web" issued on Jun. 30, 2009, U.S. Pat. No. 7,172,801 entitled "Tufted Laminate Web" issued on Feb. 6, 2007, or U.S. Pat. No. 8,440,286 entitled "Capped Tufted Laminate Web" issued on May 14, 2013. The primary topsheet may have an inverse textured web as described in U.S. Pat. No. 7,648,752 entitled "Inverse Textured Web" issued on Jan. 19, 2010. Tufts are also described in U.S. Pat. No. 7,410,683 entitled "Tufted Laminate Web" issued on Aug. 12, 2008.

The primary topsheet may have a pattern of discrete hair-like fibrils as described in U.S. Pat. No. 7,655,176 entitled "Method of Making a Polymeric Web Exhibiting A Soft and Silky Tactile Impression" issued on Feb. 2, 2010 or U.S. Pat. No. 7,402,723 entitled "Polymeric Web Exhibiting A Soft And Silky Tactile Impression" issued on Jul. 22, 2008.

The primary topsheet may comprise one or more structurally modified zones as described in U.S. Pat. No. 8,614,365 entitled "Absorbent Article" issued on Dec. 24, 2013. The primary topsheet may have one or more out of plane deformations as described in U.S. Pat. No. 8,704,036 entitled "Sanitary Napkin for Clean Body Benefit" issued on Apr. 22, 2014. The primary topsheet may have a masking composition as described in U.S. Pat. No. 6,025,535 entitled "Topsheet For Absorbent Articles Exhibiting Improved Masking Properties" issued on Feb. 15, 2000.

Another suitable primary topsheet or a primary topsheet combined with a secondary topsheet may be formed from a three-dimensional substrate as detailed in a U.S. provisional patent application No. 62/306,676 filed on Mar. 11, 2016 in the name of Jill M. Orr and entitled "A Three-Dimensional Substrate Comprising a Tissue Layer". This three-dimensional substrate has a first surface, a second surface, land areas and also comprises three-dimensional protrusions extending outward from the second surface of the three-dimensional substrate, wherein the three-dimensional protrusions are surrounded by the land areas. The substrate is a laminate comprising at least two layers in a face to face relationship, the second layer is a tissue layer facing outward from the second surface of the three-dimensional substrate, and the tissue layer comprises at least 80% pulp fibers by weight of the tissue layer.

The primary topsheet may have comprises one or more layers, for example a spunbond-meltblown-spunbond material. The primary topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997. Additional lateral extensibility in the chassis 20 (i.e., in the primary topsheet and/or the backsheet) may be provided in a variety of ways. For example, either the primary topsheet or backsheet may be pleated by any of many known methods. Alternatively, all or a portion of the chassis (i.e., also the primary topsheet and/or backsheet) may be made of a formed web material or a formed laminate of web materials like those described in U.S. Pat. No. 5,518,801 issued on 21 May 1996 in the name of Chappell et al. Such a formed web material includes distinct laterally extending regions in which the original material has been altered by embossing or another method of deformation to create a pattern of generally longitudinally oriented alternating ridges and valleys. The formed web material also includes laterally extending unaltered regions located between the laterally extending altered regions.

Secondary Topsheet

As noted previously, the disposable absorbent articles of the present disclosure may comprise additional layers, one of which includes a secondary topsheet. As mentioned previously, the secondary topsheet may be separate and apart from the absorbent system. Additionally, the secondary topsheet is disposed beneath the primary topsheet 203 and on the body-facing surface of the system. In some forms, the secondary topsheet may have a basis weight from about 40 gsm to about 100 gsm, from about 45 gsm to about 75 gsm, or from about 50 gsm to about 60 gsm, specifically including all values within these ranges and any ranges created thereby. In some forms, the secondary topsheet may comprise a homogeneous mix of fibers.

Exemplary secondary topsheets are described in additional detail in U.S. Pat. Nos. 10,532,123 and 10,307,309; U.S. Patent Application Publication Nos. 2019/0247244; 2018/0098893; and 2020/0306099.

Backsheet

The backsheet 207 of the chassis 20 may be positioned adjacent a garment-facing surface of the absorbent system 205 and may be joined thereto by attachment methods (not shown) such as those well known in the art. For example, the backsheet 207 may be secured to the absorbent system 205 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art. Forms of the present disclosure are also contemplated wherein the absorbent system 205 is not joined to the backsheet 207, the topsheet 203, or both.

The backsheet 207 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 207 may prevent, or at least inhibit, the exudates absorbed and contained in the absorbent system 205 from wetting articles of clothing which contact the incontinence pad 10 such as undergarments. However, in some instances, the backsheet 207 may permit vapors to escape from the absorbent system 205 (i.e., is breathable) while in other instances the backsheet 207 may not permit vapors to escape (i.e., non-breathable). Thus, the backsheet 205 may comprise a polymeric film such as thermoplastic films of polyethylene or polypropylene. A suitable material for the backsheet 207 is a thermoplastic film having a thickness of from about 0.012 mm (0.5 mil) to about 0.051 mm (2.0 mils), for example. Any suitable backsheet known in the art may be utilized with the present invention.

The backsheet 207 acts as a barrier to any absorbed bodily fluids that may pass through the absorbent system 205 to the garment surface thereof with a resulting reduction in risk of staining undergarments or other clothing. Further, the barrier properties of the backsheet permit manual removal, if a wearer so desires, of the interlabial absorbent article with reduced risk of hand soiling. A preferred material is a soft, smooth, compliant, liquid and vapor pervious material that provides for softness and conformability for comfort, and is low noise producing so that movement does not cause unwanted sound.

The backsheet may comprise a wet laid fibrous assembly having a temporary wet strength resin incorporated therein as described in U.S. Pat. No. 5,885,265 (Osborn, III.) issued Mar. 23, 1999. The backsheet may further be coated with a water resistant resinous material that causes the backsheet to become impervious to bodily fluids without impairing the spreading of adhesive materials thereon.

Another suitable backsheet material is a polyethylene film having a thickness of from about 0.012 mm (0.5 mil) to about 0.051 mm (2.0 mils). The backsheet may be embossed and/or matte finished to provide a more cloth-like appearance. Further, the backsheet may permit vapors to escape from the absorbent system (i.e., the backsheet is breathable) while still preventing body fluids from passing through the backsheet. A preferred microporous polyethylene film which is available from Tredegar Corporation, Virginia, USA, under Code No. XBF-1 12 W.

For a stretchable but non-elastic backsheet, one material can be used is a hydrophobic, stretchable, spun laced, non-woven material having a basis weight of from about 30 to 40 g/m2, formed of polyethylene terephthalate or polypropylene fibers. This material is breathable, i.e. permeable to water vapor and other gases.

For an elastic backsheet, one material which can be used is an elastic film sold under the trade mark EXX500 by Exxon Corporation. The material of this film is formed from an elastomeric base composition consisting of a styrene block copolymer. However, this material is not breathable. Another material which can be used for an elastic backsheet is a plastic film that has been subjected to a process that provides it with elastic-like properties without attaching elastic strands to the film, and may for example comprise a formed film made in accordance with U.S. Pat. No. 4,342,314 (Radel et al) and U.S. Pat. No. 4,463,045 (Ahr et al).

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness. Suitable single layer breathable backsheets for use herein include those described for example in GB A 2184 389, GB A 2184 390, GB A 2184 391, U.S. Pat. Nos. 4,591,523, 3,989,867, 3,156,242 and WO 97/24097.

The backsheet may have two layers: a first layer comprising a gas permeable aperture formed film layer and a second layer comprising a breathable microporous film layer as described in U.S. Pat. No. 6,462,251 (Cimini) issued Oct. 8, 2002. Suitable dual or multi-layer breathable backsheets for use herein include those exemplified in U.S. Pat. Nos. 3,881,489, 4,341,216, 4,713,068, 4,818,600, EP 203 821, EP 710 471, EP 710 472, and EP 793 952.

The backsheet may be a relatively hydrophobic 18 grams per square meter (gsm) spunbonded nonwoven web of 2 denier polypropylene fibers. The backsheet may also be a laminate as is known in the art.

The backsheet may be vapor permeable as described in U.S. Pat. No. 6,623,464 (Bewick-Sonntag) issued Sep. 23, 2003 or U.S. Pat. No. 6,664,439 (Arndt) issued Dec. 16, 2003. The backsheet can be formed from any vapor permeable material known in the art. Backsheet can be a microporous film, an apertured formed film, or other polymer film that is vapor permeable, or rendered to be vapor permeable, as is known in the art.

The backsheet may be a nonwoven web having a basis weight between about 20 gsm and about 50 gsm. In one embodiment, the backsheet is a relatively hydrophobic 23 gsm spunbonded nonwoven web of 4 denier polypropylene fibers available from Fiberweb Neuberger, under the designation F102301001. The backsheet may be coated with a non-soluble, liquid swellable material as described in U.S. Pat. No. 6,436,508 (Ciammaichella) issued Aug. 20, 2002.

The backsheet has a garment-facing side and an opposite body-facing side. The garment-facing side of the backsheet comprises a non-adhesive area and an adhesive area. The adhesive area may be provided by any conventional means. Pressure sensitive adhesives have been commonly found to work well for this purpose.

Absorbent System

The absorbent system 205 of the present invention may comprise any suitable shape including but not limited to an oval, a discorectangle, a rectangle, an asymmetric shape, and an hourglass. For example, in some forms of the present invention, the absorbent system 205 may comprise a contoured shape, e.g. narrower in the intermediate region than in the end regions. As yet another example, the absorbent system may comprise a tapered shape having a wider portion in one end region of the pad which tapers to a narrower end region in the other end region of the pad. The absorbent system 205 may comprise varying stiffness in the MD and CD.

As detailed earlier, the absorbent system 205 comprises a first absorbent core and a second absorbent core. Both are generally compressible, conformable, non-irritating to the wearer's skin, and capable of absorbing and retaining liquids such as urine and other certain body exudates including menses.

The configuration and construction of the absorbent system 205 may vary (e.g., the absorbent system 205 may have varying caliper zones, a hydrophilic gradient, a superabsorbent gradient, or lower average density and lower average basis weight acquisition zones). Further, the size and absorbent capacity of the absorbent system 205 may also be varied to accommodate a variety of wearers. However, the total absorbent capacity of the absorbent system 205 should be compatible with the design loading and the intended use of the disposable absorbent article or incontinence pad 10.

In some forms of the present invention, the absorbent system 205 may comprise a plurality of multi-functional layers that are in addition to the first and second absorbent cores. For example, the absorbent system 205 may comprise a core wrap (not shown) useful for enveloping the first and/or second absorbent cores and other optional layers. The core wrap may be formed by two nonwoven materials, substrates, laminates, films, or other materials. In a form, the core wrap may only comprise a single material, substrate, laminate, or other material wrapped at least partially around itself.

The absorbent system 205 of the present disclosure may comprise one or more adhesives, for example, to help immobilize the SAP or other absorbent materials within the first and second absorbent cores.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen. These may be used to configure the superabsorbent layers.

Additions to the system of the present disclosure are envisioned. In particular, potential additions to the current multi-laminate absorbent system are described in U.S. Pat. No. 4,610,678, entitled "High-Density Absorbent Structures" issued to Weisman et al., on Sep. 9, 1986; U.S. Pat. No. 4,673,402, entitled "Absorbent Articles With Dual-Layered Cores", issued to Weisman et al., on Jun. 16, 1987; U.S. Pat. No. 4,888,231, entitled "Absorbent Core Having A Dusting Layer", issued to Angstadt on Dec. 19, 1989; and U.S. Pat. No. 4,834,735, entitled "High Density Absorbent Members Having Lower Density and Lower Basis Weight Acquisition Zones", issued to Alemany et al., on May 30, 1989. The absorbent system may further comprise additional layers that mimic the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345. These are useful to the extent they do not negate or conflict with the effects of the below described absorbent cores of the present invention.

First Absorbent Core and Second Absorbent Core

The first and/or second absorbent cores may have cross-direction widths that are the same as each other or different. For instance, the first absorbent core may have a lesser cross-direction width than said second absorbent core or a greater cross-direction width than said second absorbent core. In certain instances, the first and second absorbent cores have machine-direction lengths that are the same while in other instances, the first and second absorbent cores have machine-direction lengths that are different. In the latter instance, the first absorbent core may have a lesser machine-direction length than the second absorbent core or conversely the first absorbent core may have a greater machine-direction length than said second absorbent core.

The first and second absorbent cores 60, 70 may further comprise an optional intermediate layer disposed between the respective superabsorbent layer and distribution layer. This optional intermediate layer may comprise materials detailed herein relative to the optional layers for the chassis, in general.

Additionally, the absorbent article or incontinence pad of the present invention may further comprise an optional laminate comprising a superabsorbent layer and a distribution layer. This optional laminate may take the form of a third, fourth, fifth, or even additional laminates. The superabsorbent layer and distribution layer may exhibit the same or different properties detailed earlier with respect to the first and second superabsorbent and distribution layers. This optional laminates may be disposed on a body-facing surface of the first laminate or second laminate or on a garment-facing surface of the first laminate or second laminate.

The first and second absorbent cores each have a first end 66, 76 that is complementary in shape to its respective second end 67, 77. More specifically, the first end 66 of the first absorbent core conforms shapewise to the second end 67 of the same absorbent core. The same conformance applies to the first end 76 of the second absorbent core relative to the second end 77 of the second absorbent core. For instance, the first end 66 of the first absorbent core fits into the second end 67 of the first absorbent core. This conformation results from a nested cut in the absorbent cores that provides matching or shape fitting ends. This is also the case for the second absorbent core's respective first 76 and second ends 77. Likewise, this feature may also be prevalent in any optional layers that might be incorporated into the absorbent system. This nesting or nested cut feature of the absorbent cores allows for reduced waste of trim during manufacture.

It has also been found that it is possible to configure the first and second absorbent cores in a manner that allows for their respective first ends to oppose one another when the first and second distribution layers are overlapped and joined forming an absorbent system with a central portion 205C comprising an overlapping area. A front end portion of the system 205F is formed from a first end 66, 76 of either the first absorbent core or the second absorbent core. A rear end portion of the system 205R is similarly formed from a first end 66, 76 of the other of the first absorbent core or the second absorbent core. This configuration yields an absorbent system with matching (i.e., a male connection) ends. The first end of each absorbent core has a male connection while the second end of each absorbent core has a female connection. In such instances, the male connection of the first end fits into (conforms to the shape of) the female connection of the second end of the same absorbent core. In another embodiment, a front end portion of the system is formed from a first end 66, 76 of either the first absorbent core or the second absorbent core while the rear end portion of the system is formed from a second end 67, 77 of the other of the first absorbent core or second absorbent core. In this instance, the second end is shaped as a female connection and therefore does not match the front end portion of the same system.

In a third embodiment, the front end portion of the system is formed from a second end of either the first absorbent core or the second absorbent core. A rear end portion of the system is similarly formed from a second end of the remaining first absorbent core or the second absorbent core. This configuration yields an absorbent system with matching (i.e., a female connection) ends. It should be noted, however, that the width of the first and second absorbent cores may be the same or different as mentioned herein. The nested cuts of the first and second ends of each of the first and second absorbent cores have shapes selected from the group consisting of arcs, semicircles, semi-ellipses, chevrons, rectangles, sinusoids, jigsaws, and combinations thereof.

In one embodiment, in addition to the topsheet and backsheet, the system may comprise the first absorbent core having a first end which is complementary in shape to its respective second end and wherein said absorbent core includes a first superabsorbent layer disposed onto a first distribution layer and a second absorbent core having a first end which is complementary in shape to its respective second end and wherein said laminate includes a second distribution layer joined to a second superabsorbent layer; wherein said first absorbent core is joined to said second absorbent core in an offset manner along a length of the absorbent article wherein the absorbent system has a front end portion that is formed by the first end of the second absorbent core.

In terms of the method of manufacture of the absorbent cores of the present invention, it has been found that it is preferred to form the first absorbent core and the second absorbent core from a web of material that is slit along its machine-direction length. Where the first absorbent core and the second absorbent core comprise laminate structures, this method is useful when the first and second superabsorbent layers are the same and the first and second distribution layers are the same. This sameness may be with regard to one or more of shape, basis weight, and material. The sameness of material for the distribution layer is preferred. Once the single laminate is slit to form the first and second laminates, these first and second laminates are joined. In a certain embodiment, the first and second laminates are joined at their respective distribution layers to the other in an offset manner as detailed herein and may be done so via standard mechanical, thermal, or chemical methods known to those skilled in the art.

Figure 5:
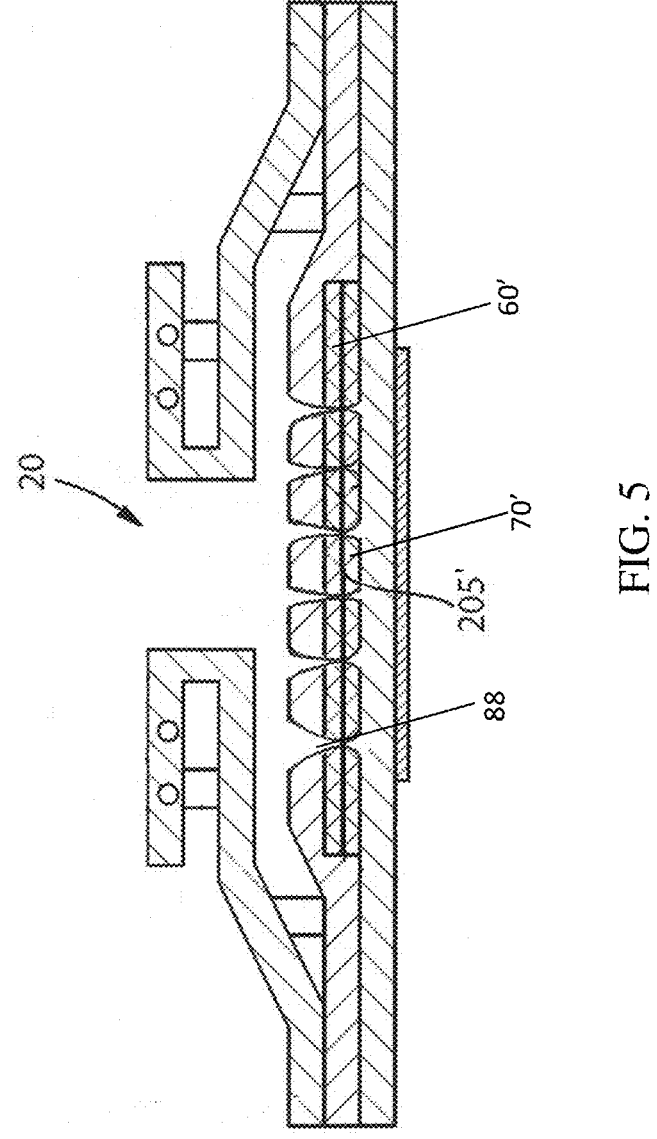
FIG. 5 is a cross-sectional view of an alternate absorbent core of the pad of FIG. 3 taken along 2-2.

In certain embodiments, the first or second absorbent cores may include one or more recessed areas that run along the machine direction or cross direction. These recessed areas may coincide with the discontinuous patterns of one or more of a superabsorbent layer and distribution layer, whether it be of the first absorbent core, second absorbent core, or both. These recessed areas may also merely be formed by embossing of the first or second absorbent cores. These recessed areas may alternatively be formed by slitting, cutting, ring-rolling, or otherwise providing mechanical deformation through the first and/or second absorbent cores. Each manner of recessed area formation mentioned herein is intended to yield a recessed area that is capable of providing a point of preferential bending of the overall article. For instance, FIG. 5 shows an alternative cross-sectional view of an alternate system 205' at 2-2 where recessed areas 88 are either gaps or embossed channels in the first and second laminates 60', 70' of absorbent system 205', in the machine direction. These recessed areas 88 need not be present in both first and second laminates 60', 70' along the entirety of each of their lengths. The recessed areas 88 may be present in the machine direction only in the overlapping joinder area of the first and second absorbent cores, 60' 70'. Alternatively, the recessed areas 88 may be present in the in the cross direction along the length of the first and second absorbent cores, 60', 70' or only in the overlapping joinder of the two cores. In instances like these, the absorbent cores through which the recessed areas are effected will be prone to bending more easily. In instances where a recessed area 88 is present in only one of a first and second absorbent cores, it is expected that there will be a preferential tendency for the pad 20 to bend at the recessed area 88. This means if the first absorbent core is closer to the body than the second absorbent core, the pad will likely bend away from the body. The opposite may be true as well in the event the second absorbent core 70' placed away from the body comprises a recessed area and the first absorbent core 60' does not. In this instance, the pad 20 may exhibit preferential tendency to bend toward the body. Depending on the overall configuration of the pad, either type of bending may be preferred in a particular instance.

Superabsorbent Layers

Where the first and second absorbent cores comprise first and second superabsorbent layers 61, 71, respectively, the first and/or second superabsorbent layers may comprise superabsorbent polymers or absorbent gelling materials (AGM). The superabsorbent layers may comprise AGM particles or AGM fibers. In general, such AGM's have been used only for their fluid-absorbing properties. Such materials form hydrogels on contact with fluid (e.g., with urine, blood, and the like). One highly preferred type of hydrogel-forming, absorbent gelling material is based on the hydrolyzed polyacids, especially neutralized polyacrylic acid. Hydrogel-forming polymeric materials of this type are those which, upon contact with fluids (i.e., liquids) such as water or body fluids, imbibe such fluids and thereby form hydrogels. In this manner, fluid discharged into the fluid absorbent structures herein can be acquired and held. These preferred superabsorbent polymers will generally comprise substantially water-insoluble, slightly cross-linked, partially neutralized, hydrogel-forming polymer materials prepared from polymerizable, unsaturated, acid-containing monomers. In such materials, the polymeric component formed from unsaturated, acid-containing monomers may comprise the entire gelling agent or may be grafted onto other types of polymer moieties such as starch or cellulose. The hydrolyzed polyacrylic acid grafted starch materials are of this latter type. Thus the preferred superabsorbent polymers include hydrolyzed polyacrylonitrile grafted starch, hydrolyzed polyacrylate grafted starch, polyacrylates, maleic anhydride-iso-butylene copolymers and combinations thereof. Especially preferred superabsorbent polymers are the hydrolyzed polyacrylates and hydrolyzed polyacrylate grafted starch.

Whatever the nature of the polymer components of the preferred superabsorbent polymers, such materials will in general be slightly cross-linked. Cross-linking serves to render these preferred hydrogel-forming absorbent materials substantially water-insoluble and cross-linking also in part determines the gel volume and extractable polymer characteristics of the hydrogels formed therefrom. Suitable cross-linking agents are well known in the art and include, for example: (1) compounds having at least two polymerizable double bonds; (2) compounds having at least one polymerizable double bond and at least one functional group reactive with the acid-containing monomer material; (3) compounds having at least two functional groups reactive with the acid-containing monomer material; and (4) polyvalent metal compounds which can form ionic cross-linkages. Preferred cross-linking agents are the di- or polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine. The cross-linking agent will generally comprise from about 0.001 mole percent to about 5 mole percent of the preferred materials.

More preferably, the cross-linking agent will comprise from about 0.01 mole percent to about 3 mole percent of the absorbent gelling materials used herein.

The preferred, slightly cross-linked, hydrogel-forming absorbent gelling materials will generally be employed in their partially neutralized form. For purposes described herein, such materials are considered partially neutralized when at least about 25 mole percent, 50 mole percent, or even 75 mole percent, of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to as the "degree of neutralization." Typically, commercial superabsorbent polymers have a degree of neutralization somewhat less than about 90%.

The preferred superabsorbent polymers used herein are those which have a relatively high capacity for imbibing fluids encountered in the fluid absorbent articles; this capacity can be quantified by referencing the "gel volume" of said superabsorbent polymers. Gel volume can be defined in terms of the amount of synthetic urine absorbed by any given fluid absorbent gelling agent buffer and is specified as grams of synthetic urine per gram of gelling agent.

Gel volume in synthetic urine can be determined by forming a suspension of about 0.1-0.2 parts of dried fluid absorbent gelling material to be tested with about 20 parts of synthetic urine. This suspension is maintained at ambient temperature under gentle stirring for about 1 hour so that swelling equilibrium is attained. The gel volume (grams of synthetic urine per gram of fluid absorbent gelling material) is then calculated from the weight fraction of the gelling agent in the suspension and the ratio of the liquid volume excluded from the formed hydrogel to the total volume of the suspension. The preferred superabsorbent polymers useful in this invention will have a gel volume of from about 20 to 70 grams, more preferably from about 30 to 60 grams, of synthetic urine per gram of absorbent gelling material.

The superabsorbent polymers hereinbefore described are typically used in the form of discrete particles. Such superabsorbent polymers can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of fluid absorbent gelling material particles may also be used.

The size of the fluid absorbent gelling material particles may vary over a wide range. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Fluid absorbent gelling material particles preferably have a particle size of from about 30 microns to about 2 mm for substantially all of the particles. "Particle Size" as used herein means the weighted average of the smallest dimension of the individual particles.

These superabsorbent layers are preferably substantially free of airfelt and are thus distinct from mixed layers that may include airfelt. As used herein, "substantially free of airfelt" means less than 5%, 3%, 1%, or even 0.5% of airfelt. In a preferred case, there will be no measurable airfelt in the superabsorbent layers. In the case of the first superabsorbent layer, it is preferably disposed onto the first distribution layer discontinuously. As used herein "discontinuously" or "in a discontinuous pattern" means that the superabsorbent polymers are applied onto the first distribution layer in a pattern of disconnected shaped areas. These areas of superabsorbent polymers or areas free of superabsorbent polymer may include, but are not limited to linear strips, non-linear strips, circles, rectangles, triangles, waves, mesh, and combinations thereof. The first superabsorbent layer like the second superabsorbent layer may, however, be disposed onto its respective distribution layer in a continuous pattern. As used herein "continuous pattern" or "continuously" means that the material is deposited and or secured to a superabsorbent carrier material and/or the adjacent distribution layer in an uninterrupted manner such that there is rather full coverage of the distribution layer by the superabsorbent polymer.

In certain embodiments, the first and second superabsorbent layers may comprise superabsorbent polymers that are the same. In other embodiments, the first and second superabsorbent layers may comprise superabsorbent polymers that are different from one another. This is may be in addition to the different deposition patterns that are discussed above.

The superabsorbent layers are disposed having a thickness of 0.2 mm, 0.3 mm, 0.4 mm, or 0.5 mm to 1 mm, 1.2 mm, 1.4 mm, 1.8 mm, or 2 mm. The first and second superabsorbent layers may have the same or different cross-direction widths as applied to their respective distribution layers. For instance, the cross-direction widths of the first and second superabsorbent layers may be from 20 mm, 25 mm, 30 mm, 35 mm, or 40 mm to 50 mm, 60 mm, 65 mm, 70 mm, 80 mm, or 90 mm. Alternatively, in embodiments where the widths of the first and second superabsorbent layers differ from one another in the cross-direction width, the first superabsorbent layer may have a lesser cross-direction width than the second superabsorbent layer. In particular, the first superabsorbent layer may have a cross-direction width that is less than about 95%, 90%, 80%, 70%, or even 60% of the width of the second superabsorbent layer.

In certain embodiments, the one or both of the first and second superabsorbent layers span greater than greater than about 50%, 60%, 70%, 80%, 90%, or even 95% of the cross-direction width of a superabsorbent carrier layer and/or the respective adjoining first or second distribution layer.

Like the optional layers that may be included in the chassis, the absorbent system may also comprise similar optional layers. They may be webs selected from the group consisting of a fibrous structure, an airlaid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof.

These optional layers of the system and of the chassis may comprise materials such as creped cellulose wadding, fluffed cellulose fibers, airfelt, and textile fibers. The materials of the optional layers may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The optional layers may be any combination of the materials listed above and/or a plurality of the materials listed above, alone or in combination.

The materials of the optional layers may be hydrophobic or hydrophilic depending on their placement within the chassis.

The materials of the optional layers may comprise constituent fibers comprising polymers such as polyethylene, polypropylene, polyester, and blends thereof. The fibers may be spunbound fibers. The fibers may be meltblown fibers. The fibers may comprise cellulose, rayon, cotton, or other natural materials or blends of polymer and natural materials. The fibers may also comprise a superabsorbent material such as polyacrylate or any combination of suitable materials. The fibers may be monocomponent, bicomponent, and/or biconstituent, non-round (e.g., capillary channel fibers), and may have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e., capillary and round) and the like. The constituent fibers may range from about 0.1 denier to about 100 denier.

The optional layers may include thermoplastic particulates or fibers. The materials, and in particular thermoplastic fibers, may be made from a variety of thermoplastic polymers including polyolefins such as polyethylene (e.g., PULPEX™) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber may be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse™ by Glyco Chemical, Inc. of Greenwich, Conn. Besides nonionic surfactants, anionic surfactants may also be used. These surfactants may be applied to the thermoplastic fibers at levels of, for example, from about 0.2 to about 1 g/cm$^2$ of thermoplastic fiber.

Suitable thermoplastic fibers may be made from a single polymer (monocomponent fibers), or may be made from more than one polymer (e.g., bicomponent fibers). The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention may include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON™, CEL-BOND™, or CHISSO™ bicomponent fibers). These bicomponent fibers may be concentric or eccentric. As used herein, the terms "concentric" and "eccentric" refer to whether the sheath has a thickness that is even, or uneven, through the cross-sectional area of the bicomponent fiber. Eccentric bicomponent fibers may be desirable in providing more compressive strength at lower fiber thicknesses. Suitable bicomponent fibers for use herein may be either uncrimped (i.e., unbent) or crimped (i.e., bent). Bicomponent fibers may be crimped by typical textile means such as, for example, a stuffer box method or the gear crimp method to achieve a predominantly two-dimensional or "flat" crimp.

The length of bicomponent fibers may vary depending upon the particular properties desired for the fibers and the web formation process. Typically, in an airlaid web, these thermoplastic fibers have a length from about 2 mm to about 12 mm long such as, for example, from about 2.5 mm to about 7.5 mm long, and from about 3.0 mm to about 6.0 mm long. Nonwoven fibers may be between 5 mm long and 75 mm long, such as, for example, 10 mm long, 15 mm long, 20 mm long, 25 mm long, 30 mm long, 35 mm long, 40 mm long, 45 mm long, 50 mm long, 55 mm long, 60 mm long, 65 mm long, or 70 mm long. The properties-of these thermoplastic fibers may also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine may have a decitex in the range from about 1.0 to about 20 such as, for example, from about 1.4 to about 10, and from about 1.7 to about 7 decitex.

The compressive modulus of these thermoplastic materials, and especially that of the thermoplastic fibers, may also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers may be used to alter the properties, and especially the density characteristics, of the respective thermally bonded fibrous matrix.

The optional layers may also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON™, and KODEL™), high melting crimped polyester fibers (e.g., KODEL™ 431 made by Eastman Chemical Co.) hydrophilic nylon (HY-DROFIL™), and the like. Suitable fibers may also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length may vary depending upon the particular properties desired for these fibers. Typically they have a length from about 0.3 to 7.5 cm, such as, for example from about 0.9 to about 1.5 cm. Suitable nonbonding thermoplastic fibers may have a decitex in the range of about 1.5 to about 35 decitex, such as, for example, from about 14 to about 20 decitex.

Distribution Layers

The first and second distribution layers are useful for wicking bodily fluids away from the skin of a wearer to facilitate comfort of continued wear after a release. The distribution layers comprise one or more of cellulose and commuted wood pulp. This may be in the form of airlaid. The airlaid may be chemically or thermally bonded. In particular, the airlaid may be multi bonded airlaid (MBAL) or hydrogen bonded airlaid (HBAL). The distribution layer may further comprise a fibrous thermoplastic adhesive material at least partially bonding the airlaid to itself and adjacent distribution layers, superabsorbent layers, or other additional (optional) layers. It should be noted that the same materials that are suitable for the optional layers of the chassis are envisioned as suitable for use in the distribution layers. The basis weight for each of the first and second distribution layers range from 80 gsm, 80 gsm, 100 gsm, 110 gsm, 120 gsm, or 130 gsm to 140 gsm, 150 gsm, 160 gsm, 180 gsm, 200 gsm, 220 gsm, or 240 gsm. A preferred basis weight is 135 gsm for each of the distribution layers of the first and second absorbent cores.

Additionally, in contrast to the superabsorbent layers described heretofore, the distribution layer(s) of the absorbent articles of the present disclosure may be substantially free of superabsorbent polymer. As used herein, "substantially free of superabsorbent polymer" means less than 5%, 3%, 1%, or even 0.5% of superabsorbent polymer.

Barrier Cuffs

The incontinence pad 10 may further comprise a first barrier cuff 230A and a second barrier cuff 230B and fastening adhesive 211 disposed on the garment-facing surface 20B of the chassis 20. As shown, the fastening adhesive 211 may not extend out laterally to the same extent as the absorbent system 205. As such, constructions where pad curl is reduced would be beneficial.

The first barrier cuff 230A and the second barrier cuff 230B may be attached to the chassis 20 in any suitable location. For example, as shown, the first barrier cuff 230A and the second barrier cuff 230B may be attached to a wearer-facing surface 20A of the chassis 20. As shown, the first barrier cuff 230A and the second barrier cuff 230B are attached to the primary topsheet 203. In some forms, the first barrier cuff 230A and the second barrier cuff 230B may be attached to a garment-facing surface 20B of the chassis 20. For example, the first barrier cuff 230A and the second barrier cuff 230B may be attached to the backsheet 207. Some examples of other suitable barrier cuffs are described in U.S. Pat. Nos. 4,695,278; 4,704,115; 4,795,454; 4,909, 803; U.S. Patent Application Publication No. 2009/0312730.

As shown, in some forms, the first barrier cuff 230A comprises a first cover 231 and a first elastic member 233. The second barrier cuff 230B comprises a second cover 235 and a second elastic member 237. As shown, the first cover 231 may fully enclose the first elastic member 233. Similarly, the second cover 235 may fully enclose the second elastic member 237.

While the first barrier cuff 230A and the second barrier cuff 230B are shown as discrete elements which are attached to the chassis 20, any suitable configuration may be utilized. For example, the first cover 231 and/or the second cover 235 may comprise a portion of the primary topsheet 203 and/or a portion of the backsheet 207. In such forms, the first barrier cuff 230A and/or the second barrier cuff 230B may be integrally formed with the chassis 20. A form where the first barrier cuff 230A and the second barrier cuff 230B are integrally formed with the chassis 20 is shown in FIG. 2 and discussed hereafter.

Referring to FIG. 2, the first elastic member 233 and the second elastic member 237 may be attached to the first cover 231 and the second cover 235, respectively, by any suitable means. In one example, the first elastic member may be adhesively attached to the first cover 231. Similarly, the second elastic member 237 may be adhesively attached to the second cover 235. For example, as shown, first adhesive portions 251 and 253 may attach the elastic members 233 and 237 to their respective covers 231 and 235. Similarly, second adhesive portions 255 and 257 may attach their respective covers 231 and 235 to the primary topsheet 203. As described below, the first elastic member 233 and the second elastic member 237 may be attached in only a portion the first cover 231 and second cover 235, respectively. Additional forms are contemplated where the first elastic member 233 and/or the second elastic member 237 are attached to the chassis 20 in conjunction with or independently from their respective covers 231 and 235.

Referring to FIG. 2, the elastic members 233 and 237 may be disposed laterally inboard of side edges 205A and 205B of the absorbent system 205. In other forms, the elastic members 233 and 237 may be disposed laterally outboard of the side edges 205A and 205B of the absorbent system 205. Still in other forms, the elastic members 233 and 237 may be disposed laterally inboard of the side edges 205A and 205B of the absorbent system 205 in the first end region 40 and the second end region 48 but laterally outboard of side edges 205A and 205B of the absorbent system 205 in the intermediate region 44. Additional forms are contemplated where the elastic members 233 and 237 are disposed laterally inboard of the side edges 205A and 205B of the absorbent system 205 in the first end region 40 but are disposed outboard of the side edges 205A and 205B of the absorbent system 205 in the intermediate region 44 and/or the second end region 48.

The elastic members comprised by the barrier cuffs can be glued in, in various glue lengths using various glues and glue amounts and placements. Placement of the glue is yet another variable which should be considered especially when designed with the system flexibility in mind. Gluing of the elastic members and the covers create anchor points on the pad.

The covers of the barrier cuffs of the present invention can be made of varying types of nonwovens of different MD and CD flexibility. The cover can be bonded to the topsheet of the absorbent article, such as, for example, by a slot coated stripe of adhesive, glue beads, ultrasonic sealing, or other suitable bonding agents. In certain forms of the present invention, the cover can be bonded to the backsheet at the side edges 22 and 24 (see FIG. 1) of the pad, such as, for example, using a crimp or other suitable bonding agents, such as, for example, adhesive.

Elastic members may comprise any suitable elastic material. Some suitable examples include Spandex™ or other similar polyurethanes, natural or synthetic rubber, styrene block copolymers, metallocene polyolefins, Lycra™, or any other suitable elastomer materials known in the art. Preferably the elastic member is durable for ease of processing and for during the use of the article and exhibits excellent elasticity (recovery after strain) even under strains as high as 400%.

Additionally, the elastic members of the present disclosure may comprise any suitable dtex. In other forms, the elastic members may comprise a dtex of 680 or less. In some forms, the elastic members may have a dtex between 680 and 470, specifically including all numbers within the range and any ranges created thereby.

Minimum spacing between the first barrier cuff 230A and the second barrier cuff 230B may be largely driven by female anatomy. However, tradeoffs can occur where the barrier cuffs (and their respective elastic members) are disposed too far outboard of the absorbent system 205 and too far inboard of the absorbent system 205. As such, spacing between the most distal elastic members of their respective barrier cuffs should be carefully selected. Starting from the narrowest width, spacing between the most distal elastic members of the first barrier cuff 230A and the second barrier cuff 230B should be large enough to allow sufficient access to the absorbent system 205 during use while also taking into account the forces which will be applied to the pad. If too narrow, access to a portion of the absorbent system 205 could be obstructed which could lead to leakage despite the barrier cuffs 230A and 230B. In some forms of the present invention, minimum spacing between the elastic member of the first barrier cuff 230A and the elastic member of the second barrier cuff 230B which are most distal to one another may be at least 20 mm. Any suitable spacing may be utilized. For example, in some forms of the present invention, the spacing may be greater than or equal to about 20 mm, greater than about 30 mm, greater than about 33 mm, greater than about 35 mm, greater than about 40 mm, greater than about 45 mm, greater than about 50 mm, greater than about 54 mm, greater than about 60 mm, greater than about 65 mm, less than or equal to about 70 mm, or less than about 65 mm, or less than about 60 mm, less than about 55 mm, less than about 50 mm, less than about 45 mm, less than about 40 mm, less than about 35 mm, less than about 30 mm, less than about 25 mm, specifically including any values within these ranges or any ranges created thereby.

Fold Lines

Yet another factor that contributes to fit is the folds or fold lines of the pad. Pads generally contain one or more folds in order to make the pad more consumer friendly and easy to transport and store. Additionally, folding the pad can reduce the likelihood of elastic creep during storage. However, these fold lines can act as bending points upon which elastomeric forces can act to deform the shape of the pad. And, similar to the anchor points discussed above, anchor points disposed too far beyond a fold line can be problematic. Anchor points disposed too far beyond a fold line can increase the torque lever arm acting on the pad in the MD direction causing pad curl and/or the pad to fold back into the folded state.

Referring back to FIG. 1, incontinence pad 10 may further comprise a first fold line 50 and a second fold line 55. The first fold line 50 can define a boundary between the first end region 40 and the intermediate region 44. The second fold line 55 can define a boundary between the second end region 48 and the intermediate region 44. The first end region 40 can be defined by the end edge 26, the first fold line 50, and a portion of the side edges 22 and 24 disposed between the end edge 26 and the first fold line 50. The intermediate area 44 can be by the first fold line 50, the second fold line 55, and a portion of the side edges 22 and 24 disposed between the first fold line 50 and second fold line 55. The second end region 48 is defined by the second fold line 55, end edge 28, and a portion of the side edges 22 and 24 disposed between the end edge 28 and the second fold line 55. The fold lines 50 and 55 can be parallel and can be co-linear (on average) with the folds which are created via the packaging process for the incontinence pad 10.

In some forms, the first fold line 50 and second fold line 55, may be configured such that the fold lines 50 and 55 dissect the pad into thirds. In other forms, the first fold line 50 may be offset toward the end edge 28, and the second fold line 55 may be offset toward the end edge 28. In such forms, this can allow the second end region 48 to be tucked between the intermediate region 44 and the first end region 40 when the pad is in the folded configuration.

Additional Features

In some forms of the present invention, the incontinence pads or sanitary napkins may comprise wings. Wings can provide additional leakage protection for the incontinence pad and can help secure the pad to the underwear of the user. Any suitable wing configuration known in the art may be utilized.

All the components can be adhered together with adhesives, including hot melt adhesives, as is known in the art. The adhesive can be Findlay H2128 UN or Savare PM 17 and can be applied using a Dynafiber HTW system.

Per FIG. 2, during use, the pad can be held in place by any support or attachment suitable for such purposes. In certain forms of the present invention, the pad is placed in the user's undergarment or panty and secured thereto by the fastening adhesive 211. The fastening adhesive 211 secures the pad in the crotch portion of the user's panty. A portion or all of the garment-facing surface 20B of the chassis 20 is coated with fastening adhesive 211. Any adhesive or glue suitable for such purposes can be used for the fastening adhesive 211 herein, such as, for example, using pressure-sensitive adhesive. Suitable adhesives include, for example, Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the absorbent article is placed in use, the pressure-sensitive adhesive is typically covered with a removable release liner in order to keep the adhesive from drying out or adhering to a surface other than the crotch portion of the panty prior to use. Suitable release liners are also described in U.S. Pat. Nos. 4,917,697 and 4,556,146. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The pad can be used by removing the release liner and thereafter placing the absorbent article in a panty so that the adhesive contacts the panty. The adhesive maintains the absorbent article in its position within the panty during use. The release liner can also be a wrapper that can individually package the pad.

Again, although the majority of discussion herein is around incontinence pads and sanitary napkins, it is envisioned that this invention is also useful for taped diapers, training pants which pull on, adult incontinence diapers and pants, and replaceable pads for incontinence and menses collection that might be inserted and removed after use in a disposable or durable panty or underpant.

What is claimed is:

1. An absorbent article comprising:
   a primary topsheet having a body-facing surface and a garment-facing surface;
   a backsheet having a body-facing surface and garment-facing surface;
   an absorbent system disposed between the primary topsheet and the backsheet, the absorbent system comprising a first absorbent core having a body-facing surface and a garment-facing surface, and a second absorbent core disposed between the first absorbent core and the backsheet, wherein the first absorbent core and the second absorbent core are in contact with each other, wherein the first absorbent core comprises a first distribution layer and a first superabsorbent layer, wherein the first superabsorbent layer forms a portion of the garment-facing surface of the first absorbent core, wherein the primary topsheet and the first absorbent core comprise one or more embossed channels including a central channel disposed on the body-facing surface of the primary topsheet, wherein each of the one or more embossed channels comprise a bottom surface subjacent to the body-facing surface of the primary topsheet, superjacent to a garment-facing surface of the first absorbent core, and superjacent to a body-facing surface of the first superabsorbent layer.

2. The absorbent article of claim 1, wherein the first distribution layer is substantially free of super absorbent polymer.

3. The absorbent article claim 1, wherein the primary topsheet and the first distribution layer comprise the one or more embossed channels such that the bottom surface is superjacent to a garment-facing surface of the first distribution layer.

4. The absorbent article claim 1, wherein the first absorbent core is joined to the second absorbent core in an offset manner along a length of the absorbent core such that a central portion of said absorbent core is formed from an overlapping joinder of said first and second absorbent cores.

5. The absorbent article of claim 4, wherein a front end portion and a rear end portion are respectively disposed at opposing ends of the central portion of the absorbent system.

6. The absorbent article of claim 1, wherein said first and second absorbent cores have different widths from one another.

7. The absorbent article of claim 1, wherein the second absorbent core comprises a second distribution layer joined to a second superabsorbent layer.

8. The absorbent article of claim 7, wherein the first superabsorbent layer is joined to said second superabsorbent layer.

9. The absorbent article of claim 7, wherein the first superabsorbent layer is joined to said second distribution layer.

10. The absorbent article of claim 7, wherein said first or second superabsorbent layers are substantially free of airfelt.

11. The absorbent article of claim 7, wherein said first and second distribution layers each comprise an airlaid material.

12. The absorbent article of claim 1, wherein said first superabsorbent layer is disposed discontinuously to the first distribution layer.

13. The absorbent article of claim 1, wherein said first and second absorbent cores each have a first end that is complementary in shape to a respective second end of the same absorbent core.

14. The absorbent article of claim 1, wherein the central channel comprises a first portion and a second portion, wherein the first portion and the second portion are discrete from one another.

15. The absorbent article of claim 1, wherein the one or more embossed channels further comprise a front region channel and a rear region channel disposed on longitudinal opposite ends of the central channel.

16. The absorbent article of claim 1, wherein the central channel has a length which is 53 percent or less than the overall length of the absorbent article.

17. The absorbent article of claim 1, wherein the central channel comprises a length of from between about 25 percent to about 53 percent of the overall length of the absorbent article.

18. The absorbent article of claim 1, wherein a front region channel and a rear region channel are disposed on opposite sides of the central channel, and wherein the overall length of the embossed channels is 80 percent or less of the overall length of the absorbent article.

19. The absorbent article of claim 18, wherein the overall length of the embossed channels is from between about 30 percent to about 80 percent of the overall length of the absorbent article.

20. An absorbent article comprising:
a primary topsheet having a body-facing surface and a garment-facing surface;
a backsheet having a body-facing surface and garment-facing surface;
an absorbent system disposed between the primary topsheet and the backsheet, the absorbent system comprising a first absorbent core having a body-facing surface and a garment-facing surface, and a second absorbent core disposed between the first absorbent core and the backsheet, wherein the first absorbent core comprises a first distribution layer and a first superabsorbent layer, wherein the first superabsorbent layer forms a portion of the garment-facing surface of the first absorbent core, wherein the primary topsheet and the first absorbent core comprise one or more embossed channels including a central channel disposed on the body-facing surface of the primary topsheet, wherein each of the one or more embossed channels comprise a bottom surface subjacent to the body-facing surface of the primary topsheet, superjacent to a garment-facing surface of the first absorbent core; wherein the primary topsheet, the first distribution layer, and the first superabsorbent layer comprise the one or more embossed channels.

* * * * *